(12) United States Patent
Blow et al.

(10) Patent No.: US 6,324,425 B1
(45) Date of Patent: Nov. 27, 2001

(54) RECHARGE CIRCUITRY FOR MULTI-SITE STIMULATION OF BODY TISSUE

(75) Inventors: Brian A. Blow, Maple Grove; Jean E. Hudson, Coon Rapids, both of MN (US); Michael B. Terry, Gersham, OR (US)

(73) Assignee: Medtronic, Inc.,, Minneapolis, MN (US)

( * ) Notice: Subject to any disclaimer, the term of this patent is extended or adjusted under 35 U.S.C. 154(b) by 0 days.

(21) Appl. No.: 09/439,568

(22) Filed: Nov. 12, 1999

Related U.S. Application Data
(60) Provisional application No. 60/114,090, filed on Jul. 28, 1999, and provisional application No. 60/145,860, filed on Jul. 28, 1999.

(51) Int. Cl.[7] ................................................. A61N 1/368
(52) U.S. Cl. .................................................. 607/13; 607/9
(58) Field of Search .............................. 607/4–5, 9, 11, 607/13, 148; 128/901–902

(56) References Cited

U.S. PATENT DOCUMENTS

| | | | |
|---|---|---|---|
| 3,937,226 | 2/1976 | Funke | 128/419 PG |
| 4,088,140 | 5/1978 | Rockland et al. | 128/419 PG |
| 4,332,259 | 6/1982 | McCorkle, Jr. | 128/786 |

(List continued on next page.)

FOREIGN PATENT DOCUMENTS

| | | | |
|---|---|---|---|
| WO 99/29368 | 6/1999 | (WO) | A61N/1/37 |

OTHER PUBLICATIONS

Daubert et al., "Permanent Left Ventricular Pacing With Transvenous Leads Inserted Into The Coronary Veins", *PACE* (vol. 21, Part II, pp. 239–245, Jan. 1998).

Cazeau et al., "Four Chamber Pacing in Dilated Cardiomyopathy", *PACE* (vol. 17, Part 11, pp. 1974–1979, Nov. 1994).

Daubert et al., "Renewal of Permanent Left Atrial Pacing via the Coronary Sinus", *PACE* (vol. 15, Part 11, NASPE Abstract 255, p. 572, Apr. 1992).

Daubert et al., "Permanent Dual Atrium Pacing in Major Intra–atrial Conduction Blocks: A Four Years Experience", *PACE* (vol. 16, Part II, NASPE Abstract 141, p. 885, Apr. 1993).

*Primary Examiner*—Kennedy Schaetzle
*Assistant Examiner*—Kristen Droesch
(74) *Attorney, Agent, or Firm*—Girma Wolde-Michael; Reed A. Duthler

(57) ABSTRACT

Multi-chamber cardiac pacing systems for providing multi-site pacing to at least one of the right and left atria and then synchronously to the right and left ventricles in a triggered pacing sequence while providing for recharge of the output capacitors of each output amplifier in the shortest time. The recharge operations of the present invention come into play when bi-chamber pacing is invoked to deliver right and left heart chamber pacing pulses that are separated by a triggered pacing delay that overlaps, i.e., is shorter than, the recharge time period. In a truncated recharge mode, the first pacing pulse is delivered through the first pacing path, and the recharging of the first pacing path is commenced for the duration of the triggered pacing delay. Then, the second pacing pulse is delivered, and the second pacing path is recharged for a second recharge period. The recharging of the first pacing path is conducted simultaneously with or after completion of the second recharge period. In a postponed and sequential mode, recharging of the first pacing path is postponed until after delivery of the second pacing pulse and recharging of the second pacing path. In a simultaneous pacing mode, recharging of the first pacing path takes place after delivery of the second pacing pulse and simultaneously with recharging of the second pacing path. This invention can be used in cardio defibrillators with pacing capabilities if desired.

30 Claims, 12 Drawing Sheets

U.S. PATENT DOCUMENTS

| | | | |
|---|---|---|---|
| 4,354,497 | 10/1982 | Kahn | 128/419 D |
| 4,373,531 * | 2/1983 | Wittkampf et al. | 607/13 |
| 4,406,286 | 9/1983 | Stein | 128/419 PG |
| 4,458,677 | 7/1984 | McCorkle, Jr. | 128/786 |
| 4,548,203 | 10/1985 | Tacker, Jr. et al. | 128/419 D |
| 4,928,688 | 5/1990 | Mower | 128/419 PG |
| 5,174,289 | 12/1992 | Cohen | 128/419 PG |
| 5,267,560 | 12/1993 | Cohen | 607/25 |
| 5,350,410 * | 9/1994 | Kleks et al. | 607/28 |
| 5,387,228 | 2/1995 | Shelton | 607/11 |
| 5,514,161 | 5/1996 | Limousin | 607/9 |
| 5,540,727 | 7/1996 | Tockman et al. | 607/18 |
| 5,584,867 | 12/1996 | Limousin et al. | 607/9 |
| 5,674,259 | 10/1997 | Gray | 607/20 |
| 5,720,768 | 2/1998 | Verbove-Nelissen | 607/9 |
| 5,728,140 | 3/1998 | Salo et al. | 607/9 |
| 5,735,880 * | 4/1998 | Prutchi et al. | 607/9 |
| 5,741,309 | 4/1998 | Maares | 607/9 |
| 5,782,880 | 7/1998 | Lahtinen | 607/9 |
| 5,792,203 | 8/1998 | Schroeppel | 607/30 |
| 5,797,970 | 8/1998 | Pouvreau | 607/9 |
| 5,902,324 | 5/1999 | Thompson et al. | 607/9 |
| 5,941,903 * | 8/1999 | Zhu et al. | 607/13 |

* cited by examiner

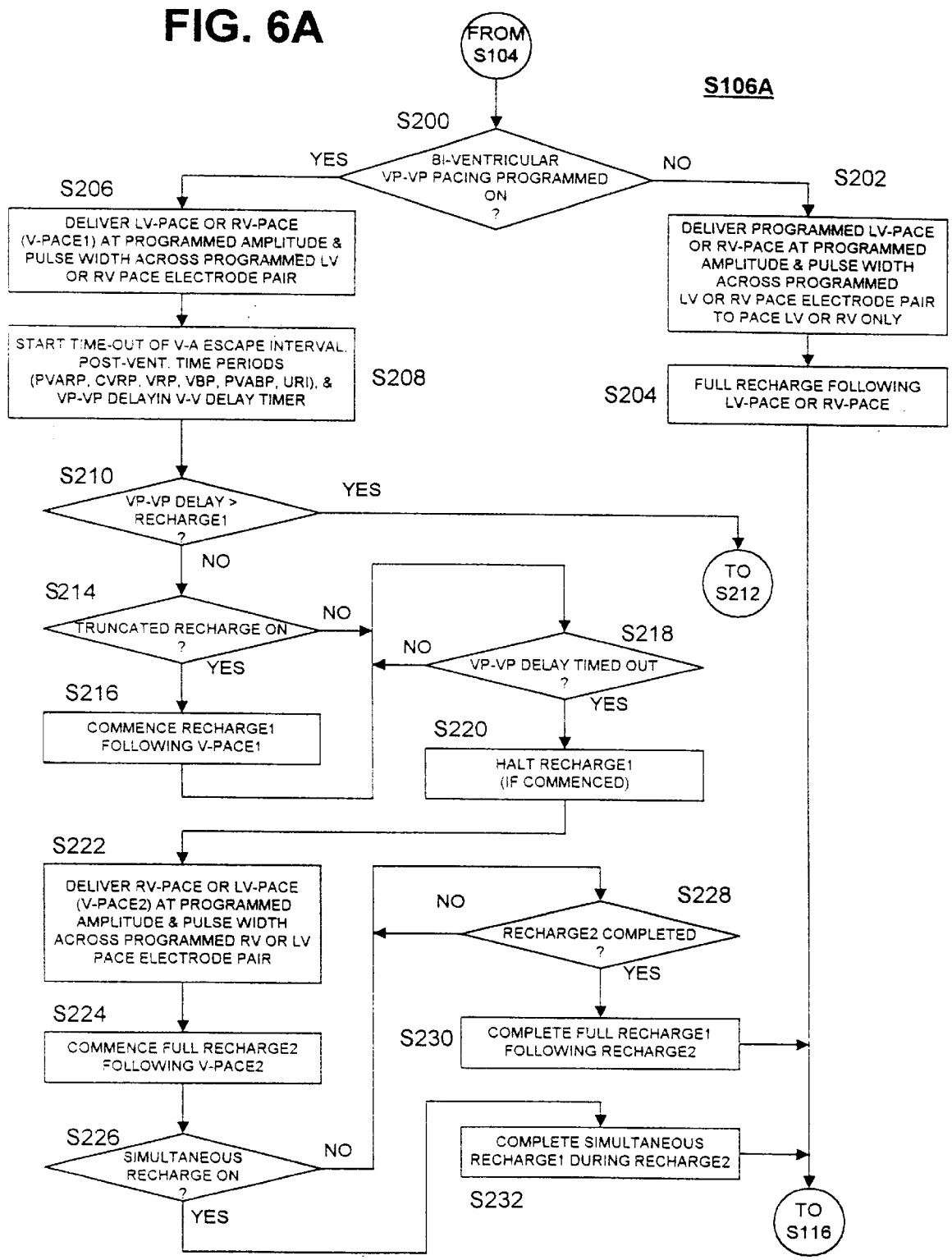

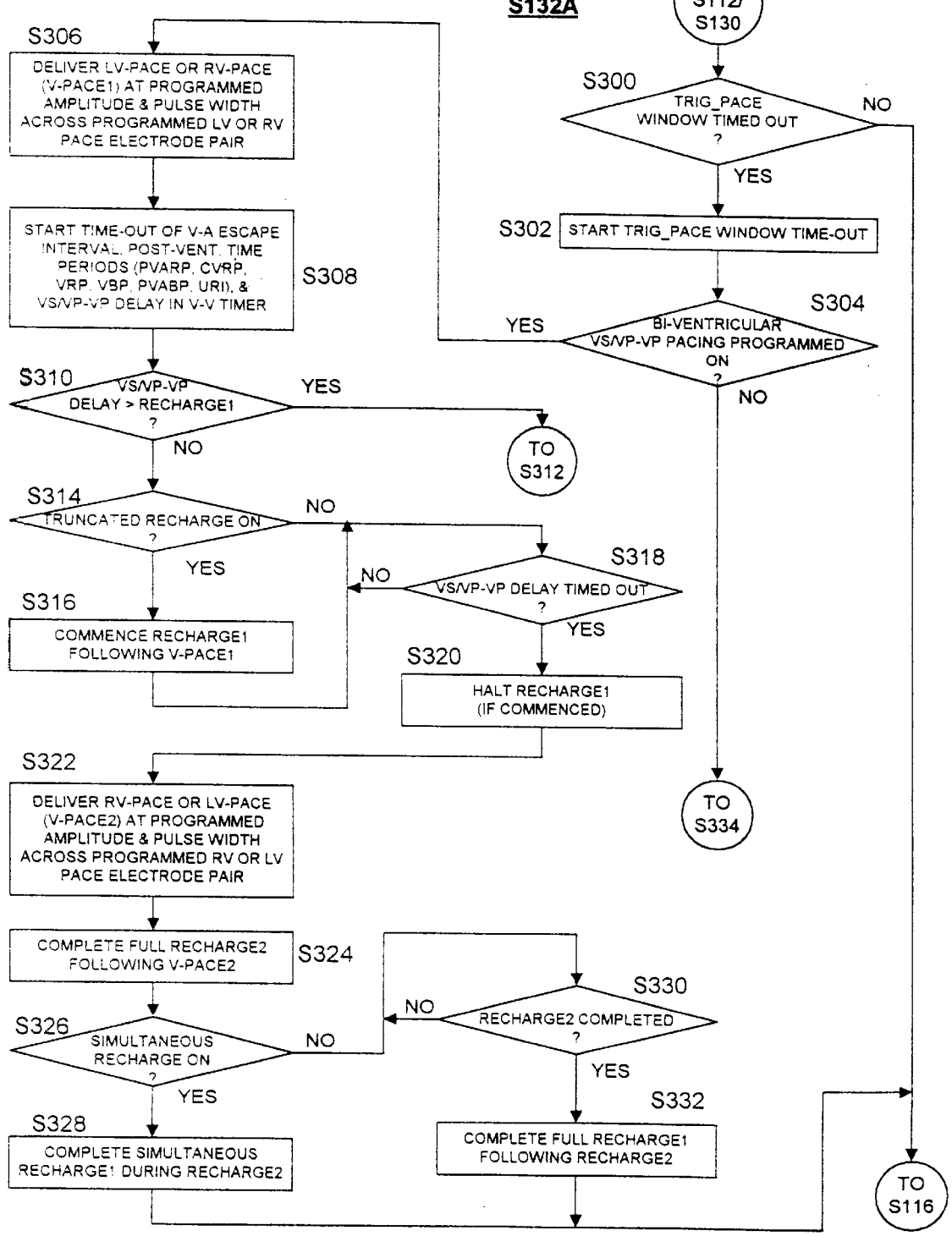

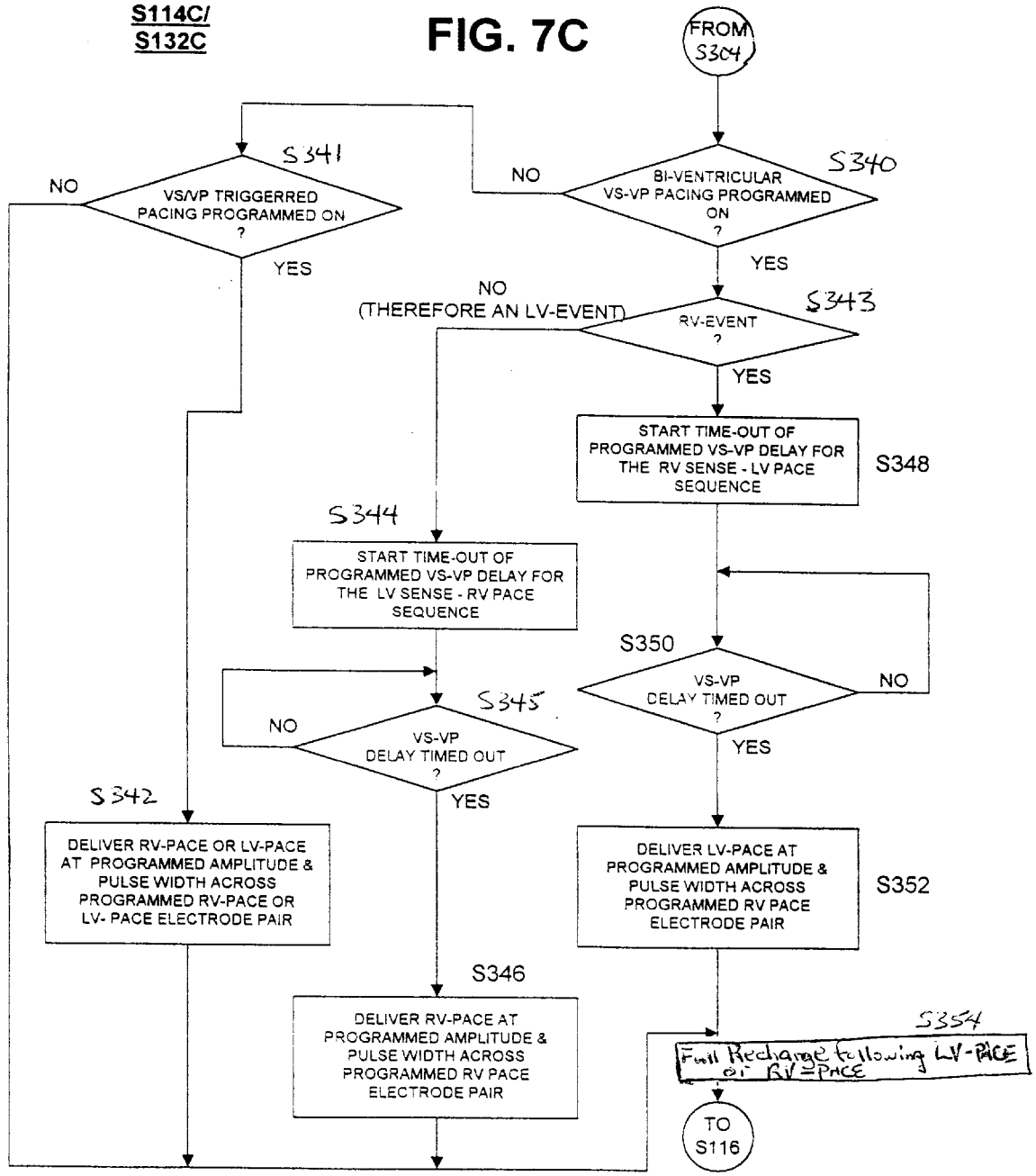

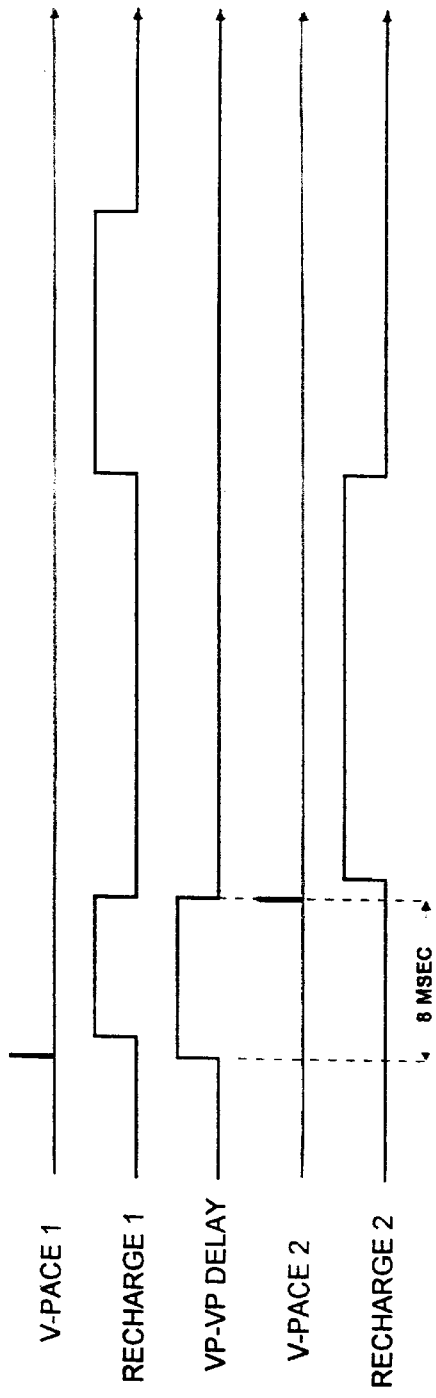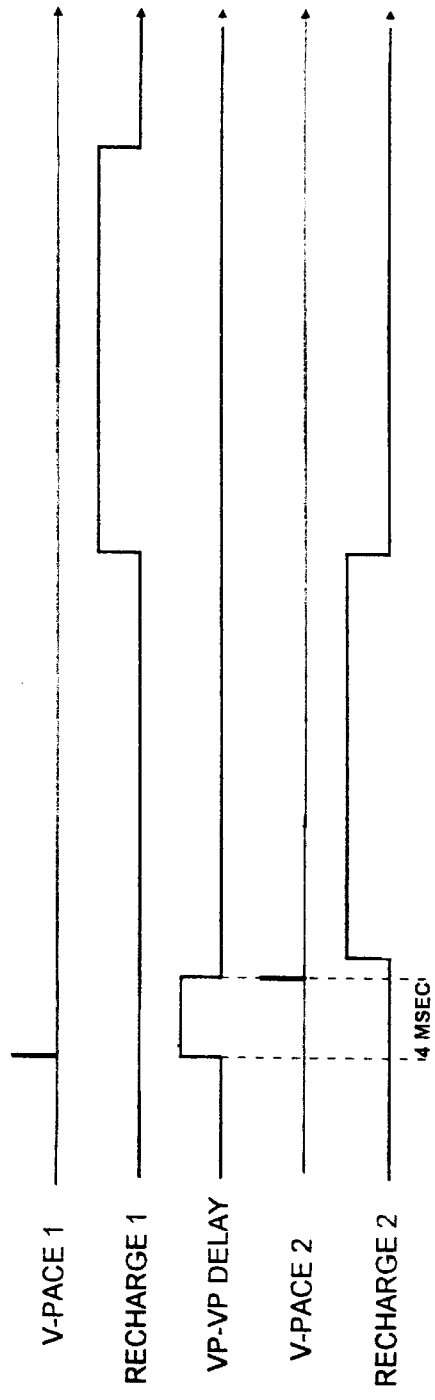

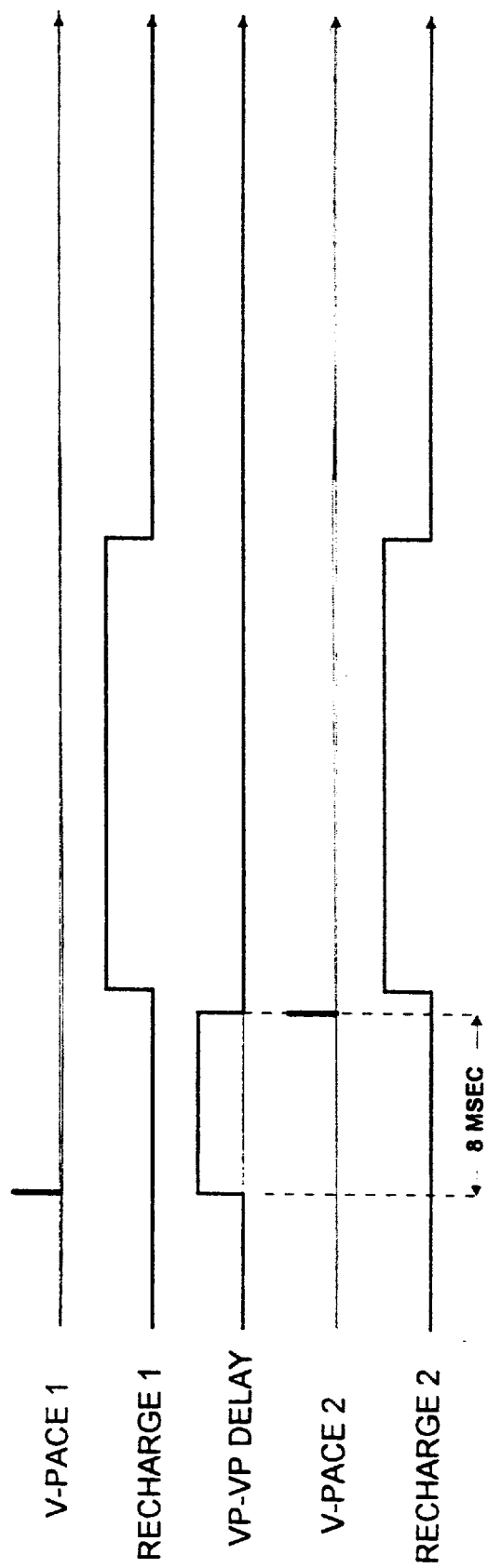

RECHARGE CIRCUITRY FOR MULTI-SITE STIMULATION OF BODY TISSUE

This patent application claims the benefit of U.S. Provisional Application Nos. 60/114,090 filed Dec. 29, 1998 and 60/145,860 filed Jul. 28, 1999.

CROSS-REFERENCE TO RELATED APPLICATIONS

Reference is hereby made to the following, commonly assigned, co-pending, U.S. Patent Applications which disclose common subject matter: U.S. Pat. No. 6,122,545 filed Apr. 28, 1998, for MULTIPLE CHANNEL, SEQUENTIAL, CARDIAC PACING SYSTEMS filed in the names of C. Struble et al.; Ser. No. 09/439,244 filed on event date herewith for MULTI-SITE CARDIAC PACING SYSTEM HAVING CONDITIONAL REFRACTORY PERIOD filed in the names of K. Kleckner et al.; Ser. No. 09/439,569 filed on even date herewith for CARDIAC PACING SYSTEM DELIVERING MULTI-SITE PACING IN A PREDETERMINED SEQUENCE TRIGGERED BY A SENSE EVENT in the names of C. Yerich et al.; Ser. No. 09/439,565 filed on even date herewith for BI-CHAMBER CARDIAC PACING SYSTEM EMPLOYING UNIPOLAR LEFT HEART CHAMBER LEAD IN COMBINATION WITH BIPOLAR RIGHT HEART CHAMBER LEAD in the names of B. Blow et al.; Ser. No. 09/439,078 filed on even date herewith for MULTI-SITE CARDIAC PACING SYSTEM HAVING TRIGGER PACE WINDOW in the names of C. Juran et al.; and Ser. No. 09/439,243 filed on even date herewith for AV SYNCHRONOUS CARDIAC PACING SYSTEM DELIVERING MULTI-SITE VENTRICULAR PACING TRIGGERED BY A VENTRICULAR SENSE EVENT DURING THE AV DELAY in the names of C. Yerich et al.

FIELD OF THE INVENTION

The present invention pertains to providing multiple, closely timed, electrical stimulation pulses to living tissue through multiple reactive stimulation paths and for recharging the stimulation paths to alleviate polarization after potentials prior to delivery of subsequent stimulation pulses to the same stimulation paths, and particularly to cardiac pacing systems for providing closely timed pacing pulses to right and left heart chambers in triggered pacing modes while providing for recharge of the pacing paths in as short a time as possible.

BACKGROUND OF THE INVENTION

In diseased hearts having conduction defects and in congestive heart failure (CHF), cardiac depolarizations that naturally occur in one upper or lower heart chamber are not conducted in a timely fashion either within the heart chamber or to the other upper or lower heart chamber. In such cases, the right and left heart chambers do not contract in optimum synchrony with each other, and cardiac output suffers due to the conduction defects. In addition, spontaneous depolarizations of the left atrium or left ventricle occur at ectopic foci in these left heart chambers, and the natural activation sequence is grossly disturbed. In such cases, cardiac output deteriorates because the contractions of the right and left heart chambers are not synchronized sufficiently to eject blood therefrom. Furthermore, significant conduction disturbances between the right and left atria can result in left atrial flutter or fibrillation.

It has been proposed that various conduction disturbances involving both bradycardia and tachycardia of a heart chamber could benefit from pacing pulses applied at multiple electrode sites positioned in or about a single heart chamber or in the right and left heart chambers in synchrony with a depolarization which has been sensed at least one of the electrode sites. It is believed that cardiac output can be significantly improved when left and right chamber synchrony is restored, particularly in patients suffering from dilated cardiomyopathy and CHF.

A number of proposals have been advanced for providing pacing therapies to alleviate these conditions and restore synchronous depolarization and contraction of a single heart chamber or right and left, upper and lower, heart chambers as described in detail in commonly assigned U.S. Pat. Nos. 5,403,356, 5,797,970 and 5,902,324 and in U.S. Pat. Nos. 5,720,768 and 5,792,203 all incorporated herein by reference. The proposals appearing in U.S. Pat. Nos. 3,937,226, 4,088,140, 4,548,203, 4,458,677, 4,332,259 are summarized in U.S. Pat. Nos. 4,928,688 and 5,674,259, all incorporated herein by reference. The advantages of providing sensing at pace/sense electrodes located in both the right and left heart chambers is addressed in the '688 and '259 patents, as well as in U.S. Pat. Nos. 4,354,497, 5,174,289, 5,267,560, 5,514,161, and 5,584,867, also all incorporated herein by reference.

The medical literature also discloses a number of approaches of providing bi-atrial and/or bi-ventricular pacing as set forth in: Daubert et al., "Permanent Dual Atrium Pacing in Major Intra-atrial Conduction Blocks: A Four Years Experience", PACE (Vol. 16, Part II, NASPE Abstract 141, p.885, April 1993); Daubert et al., "Permanent Left Ventricular Pacing With Transvenous Leads Inserted Into The Coronary Veins", PACE (Vol. 21, Part II, pp. 239–245, January 1998); Cazeau et al., "Four Chamber Pacing in Dilated Cardiomyopathy", PACE (Vol. 17, Part II, pp. 1974–1979, November 1994); and Daubert et al., "Renewal of Permanent Left Atrial Pacing via the Coronary Sinus", PACE (Vol. 15, Part II, NASPE Abstract 255, p. 572, April 1992), all incorporated herein by reference.

Problems surface in implementing multi-site pacing in a single heart chamber or in right and left heart chamber pacing within the contexts of conventional timing and control systems for detecting sense event signals generated by sense amplifiers coupled to spaced apart pace/sense electrodes. The application of closely timed pacing pulses to the right and left heart chamber or at spaced apart sites in the same heart chamber and the detection of conducted depolarizations are complicated due to other actions that must be taken after delivery of pacing pulses to allow sense amplifiers to be reconnected to the sense/pace electrodes in as short a time as possible.

Typically, a negative-going or cathodal voltage pacing pulse is applied to a small surface area, active pace/sense electrode, which is typically the tip electrode of an endocardial lead lodged against the heart tissue. The pacing pulse is produced by the exponential discharge of an output capacitor through the impedance load in the pacing path including a coupling capacitor, the pace electrodes, and the patient's heart tissue between the pace electrodes.

Immediately following delivery of a pacing pulse to cardiac tissue, a residual post-pace polarization signal (or "after-potential") remains in the pacing path due to the residual energy in the impedance load into which the output capacitor is discharged to deliver the pacing pulse. The impedance load across the output amplifier terminals comprises the impedance of the coupling capacitor, the lead conductor(s), the tissue-electrode interface impedances, and the impedance of the body tissue bulk between the active and indifferent electrodes. The impedances of the body tissue and the lead conductor(s) may be modeled as a simple series bulk resistance, leaving the tissue-electrode interfaces and any coupling capacitors as the reactive energy absorbing/discharging elements of the total load. There are typically two tissue-electrode interfaces in a pacing path, one at the active tip electrode, and one at the indifferent ring (or IPG case or "can") electrode. The energy stored in these interfaces and any coupling capacitors dissipates after the pacing pulse through the pacing path impedance load creating the after-potential that can be sensed at each electrode and affect the ability of the sense amplifiers to sense natural or evoked cardiac events. The tip electrode is the primary after-potential storage element in comparison to the case and ring electrodes. An indifferent ring electrode typically stores more energy than does a can electrode due to differences in electrode areas.

In conventional pacing systems, the sense amplifiers are "blanked", i.e., uncoupled, from the pace/sense electrodes during the delivery of the pacing pulse and for a programmed blanking period thereafter until the repolarization of the tissue-electrode interfaces operation takes place. Most current pacemaker output amplifiers circuits incorporate "fast recharge" circuitry for short circuiting the pacing path and actively dissipating or countering after-potentials during the blanking of the sense amplifier's input terminals to shorten the time that it would otherwise take to dissipate afterpotentials. Fast recharge circuitry and operations are described in commonly assigned U.S. Pat. Nos. 4,406, 286, 5,782,880, and German OLS DE 196 15 159, all incorporated herein by reference. The primary purposes of providing a recharge operation are to ensure that the coupling capacitor(s) is recharged to an insignificant voltage level or equilibrium prior to the delivery of the next pacing pulse through it and to allow the net DC current in the pacing path to settle to zero to facilitate sensing in the same pacing path or using one of the pace/sense electrodes of that pacing path.

In the case of bi-chamber pacing of the type described in the above-incorporated '324 patent, for example, it is desirable to be able to deliver first and second pacing pulses through independent output amplifier circuits in close spacing, which has been suggested to be as short as 0 msec to 80 msec. We have discovered that the pacing discharge and recharge circuits for each such pacing pulse can overlap one another and interfere with coupled pacing under certain circumstances. This interference can prevent the delivery of simultaneous pacing pulses and limit the minimum delay between the delivery of the right and left chamber pacing pulses to the recharge time for the first delivered pacing pulse.

Similar problems arise in delivering closely spaced pacing pulses to multiple sites in the same heart chamber and recharging the multiple pacing pathways. Moreover, these problems arise in providing multiple, closely timed, electrical stimulation pulses to living tissue through multiple reactive stimulation paths where recharging the stimulation paths is necessary to alleviate polarization after potentials prior to delivery of subsequent stimulation pulses to the same stimulation paths.

SUMMARY OF THE INVENTION

In its broad aspects, the present invention is directed to repetitively delivering first and second closely spaced electrical stimulation pulses to living tissue through first and second reactive stimulation paths and for recharging the stimulation paths to alleviate polarization after potentials prior to delivery of subsequent stimulation pulses to the same stimulation paths.

In the context of the above-described problems with delivery of closely spaced pacing pulses, the present invention is directed in one specific aspect to providing multi-site and right and left heart chamber pacing systems and methods of operation that allow for a wide selection of pacing and sensing paths or vectors with separate or shared indifferent electrodes and allow recharging of the pacing paths in as short a time as possible.

The recharge operations of the present invention come into play in one preferred embodiment when bi-chamber pacing is invoked to deliver right and left heart chamber pacing pulses that are separated by a triggered pacing delay that overlaps, i.e., is shorter than, the recharge time period. In a truncated recharge mode, the first pacing pulse is delivered through the first pacing path, and the recharging of the first pacing path is commenced for the duration of the triggered pacing delay. Then, recharging of the first pacing path is halted, the second pacing pulse is delivered, and the second pacing path is recharged for a second recharge period. The recharging of the first pacing path is conducted simultaneously with or after completion of the second recharge period. In a postponed and sequential mode, recharging of the first pacing path is postponed until after delivery of the second pacing pulse and recharging of the second pacing path. In a simultaneous pacing mode, recharging of the first pacing path takes place after delivery of the second pacing pulse and simultaneously with recharging of the second pacing path.

The present invention provides recharge sequences that can be applied to a wide variety of other pacing systems or other human tissue stimulators that provide closely spaced pacing or other stimulation pulses into pacing paths or stimulation paths that require recharging prior to the delivery of a subsequent pacing or stimulation pulse.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIGS. 6A–6B are a flow chart illustrating the steps of delivering ventricular pacing pulses following time-out of an AV delay in FIG. 4;

FIGS. 7A–7C are a flow chart illustrating the steps of delivering ventricular pacing pulses following a ventricular sense event during the time-out of an AV delay or the V-A escape interval in FIG. 4;

FIGS. 9–12 illustrate recharge modes of the present invention for avoiding the error conditions of FIG. 8.

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. For example, the preferred embodiment of the invention is disclosed in the context of a multi-channel pacing system operating in demand, atrial tracking, and triggered pacing modes for restoring synchrony in depolarizations and contraction of left and right heart chambers for treating bradycardia in those chambers. The invention is described below in the context of a three channel pacing system having an AV synchronous operating mode for restoring upper and lower heart chamber synchronization and right and left ventricular chamber depolarization synchrony. But, the invention can be practiced in a two channel or four channel pacing system of the type disclosed in the above-incorporated '324 patent as well. Moreover, the invention can be practiced in a pacemaker providing pacing and sensing at multiple spaced apart pace/sense electrode sites in a single heart chamber.

The present invention avoids complications arising from recharging the coupling capacitances and dissipating tissue-impedance charges that remain after delivery of a pacing pulse to ready the pace/sense electrodes for sensing and pacing by use of rules of delivery of pacing pulses and recharging the pacing path depending upon the selection of pace and sense electrode pairs and the V-V triggered pacing delay between delivered bi-chamber pacing pulses.

It should also be appreciated that the recharge system of the present invention may be incorporated into an anti-tachyarrhythmia system including specific high rate pacing and cardioversion shock therapies for providing staged therapies to treat a diagnosed arrhythmia. Moreover, the recharge system of the present invention may be implemented in other tissue stimulators that repetitively deliver first and second closely spaced electrical stimulation pulses to living tissue through first and second reactive stimulation paths requiring recharging.

Figure 1:
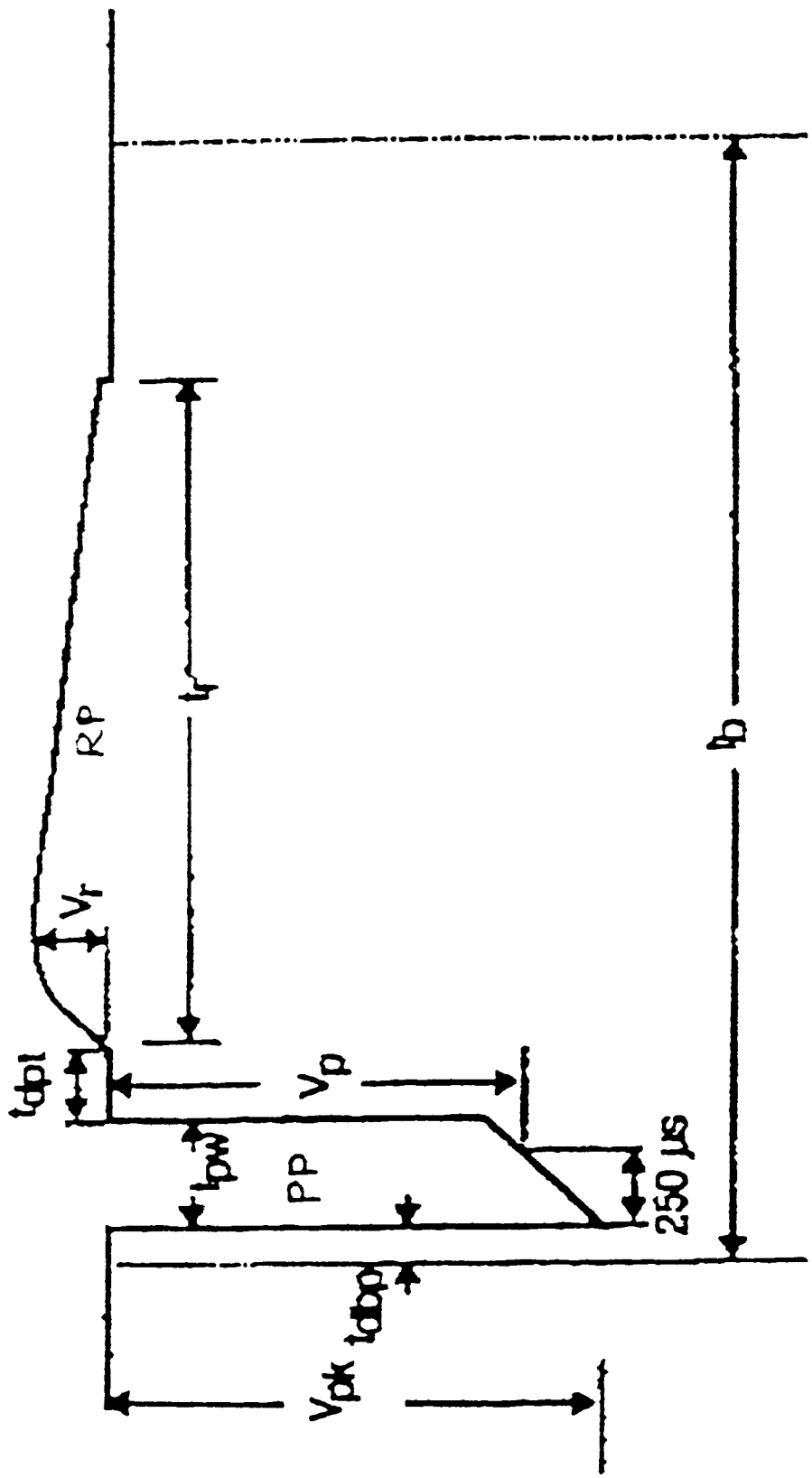
FIG. 1 is an illustration of the idealized waveform of a typical pacing pulse delivered to the patient's heart, and the after-potential that persists following termination of the pacing pulse.
Figure 2:
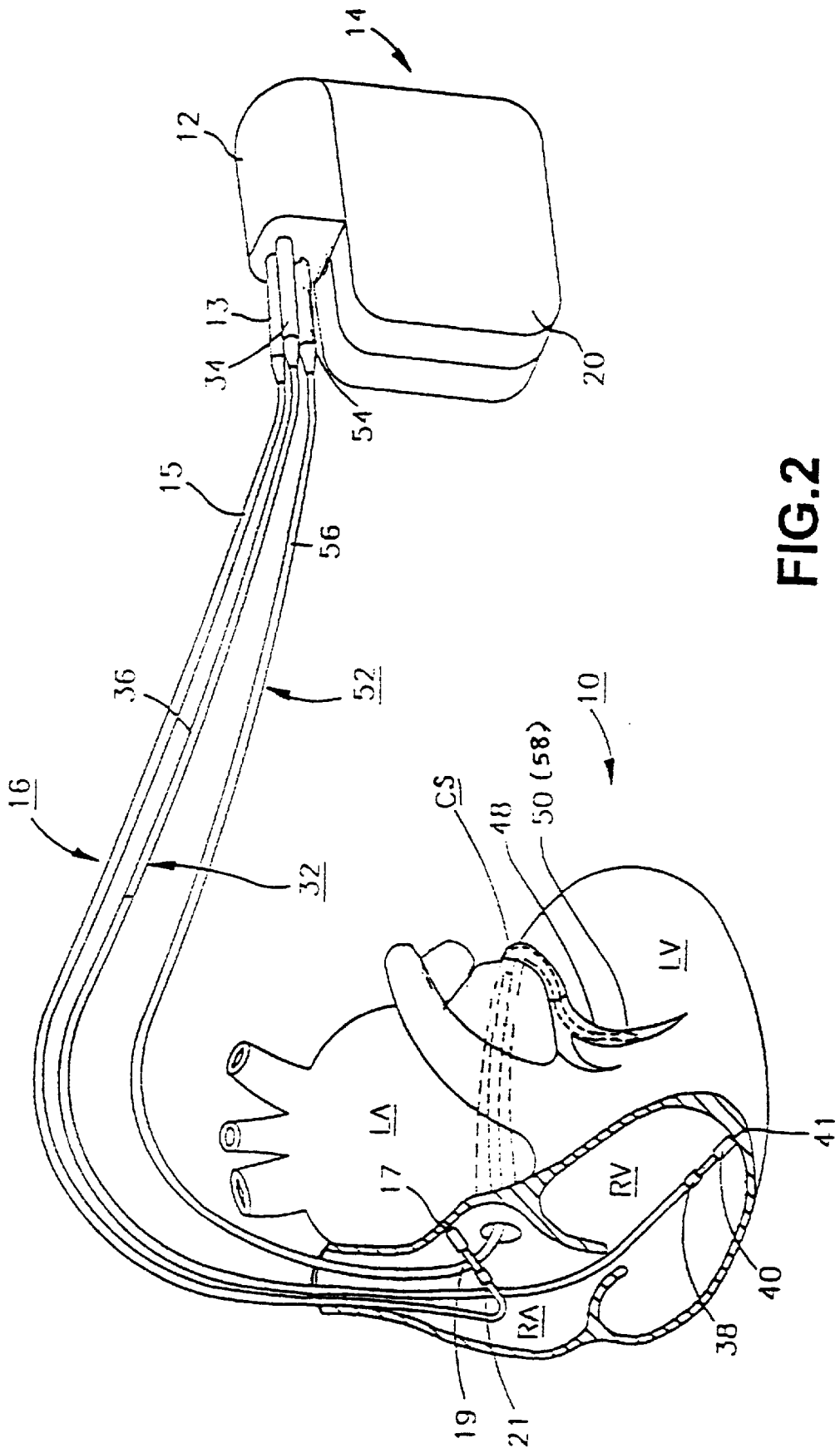
FIG. 2 is a schematic diagram depicting a three channel, atrial and bi-ventricular, pacing system in which the present invention is preferably implemented.

FIG. 1 shows a negative-going or cathodal voltage pacing pulse (PP) applied to a small surface area, active pace/sense electrode, which is typically the tip electrode of an endocardial lead lodged against the heart tissue as shown in FIG. 2, for example. The pacing pulse PP is produced by the exponential discharge of an output capacitor through the impedance load in the pacing path including a coupling capacitor, the pace electrodes, and the patient's heart tissue between the pace electrodes. The peak (i.e., most negative) leading edge pacing pulse voltage amplitude is designated in FIG. 1 as $V_{pk}$. The leading edge amplitude $V_{pk}$ falls off as the capacitor is discharged over the pulse width $t_{pw}$. The pacing pulse width of PP is designated as $t_{pw}$, and it corresponds to the time interval during which the output capacitor is coupled to the active and indifferent electrodes through the pacing path. The pacing pulse amplitude, measured at a point 250 μSec after the start of PP is designated as $V_p$ in FIG. .1.

After a time delay $t_{dpr}$, the pacing path is short circuited for the recharge time period $t_r$ to allow the polarization after-potentials to dissipate. The decaying recharge voltage wave RP having a regulated peak voltage $V_r$ can be observed across the pacing path during the recharge time period $t_r$. The sense amplifier coupled to the active electrode and other sense amplifiers in the pacing system are blanked during a blanking period $t_b$ that is somewhat longer than the recharge time period $t_r$. The recharge time period $t_r$ may continue for 10–30 msec to recharge the pacing path, i.e., to dissipate the residual after-potentials.

FIG. 2 is a schematic representation of an implanted, three channel cardiac pacemaker of the above noted types for restoring AV synchronous contractions of the atrial and ventricular chambers and simultaneous or sequential pacing of the right and left ventricles. The pacemaker IPG 14 is implanted subcutaneously in a patient's body between the skin and the ribs. Three endocardial leads 16, 32 and 52 connect the IPG 14 with the RA, the RV and the LV, respectively. Each lead has at least one electrical conductor and pace/sense electrode, and a remote indifferent electrode 20 is formed as part of the outer surface of the housing of the IPG 14. As described further below, the pace/sense electrodes and the remote indifferent electrode 20 (IND_CAN electrode) can be selectively employed to provide a number of unipolar and bipolar pace/sense electrode combinations for pacing and sensing functions. The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a unipolar, endocardial LV CS lead 52 is passed through a vein and the RA chamber of the heart 10, into the CS and then inferiorly in a coronary venous branch 48 to extend the distal LV CS pace/sense electrode 50 alongside the LV chamber. The LV CS lead 52 is formed with a small diameter single conductor lead body 56 coupled at the proximal end connector 54 fitting into a bore of IPG connector block 12. A small diameter unipolar lead body 56 is selected in order to place the distal LV CS pace/sense electrode 50 in a vein branching inferiorly from the coronary sinus 48.

Certainly other types of leads could substitute for the unipolar CS lead, for example, epicardial leads or even patch electrodes which may serve double duty as defibrillation electrodes when needed could be used, as may be desireable in a particular patient.

Figure 3:
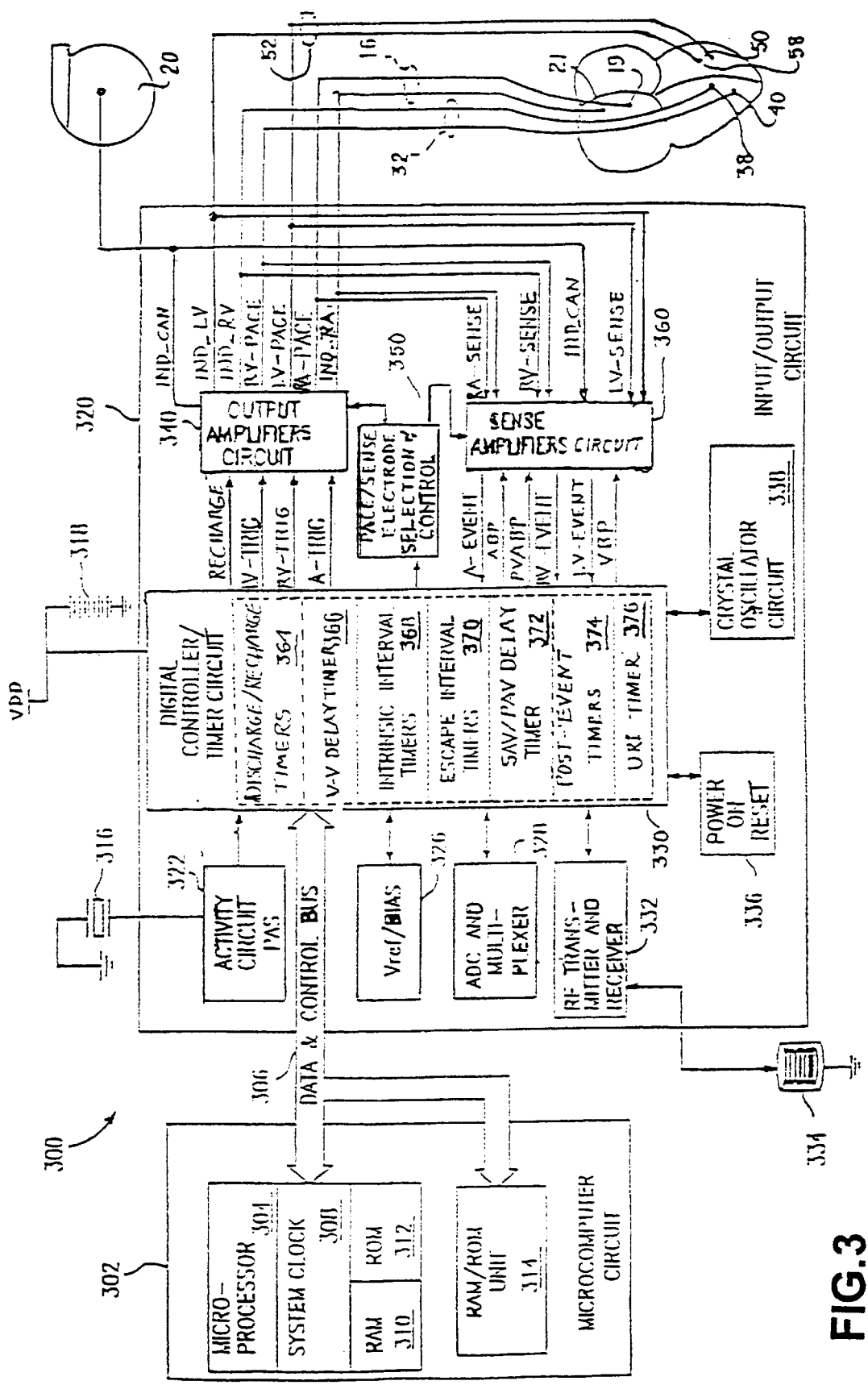
FIG. 3 is a simplified functional block diagram of one embodiment of IPG circuitry and associated leads employed in the system of FIG. 2 for providing three pacing channels that are selectively programmed for selectively pacing and sensing depolarizations of the right and left ventricles in synchrony with pacing and sensing depolarizations of the atria.

The distal LV CS pace/sense electrode 50 can be paired with the proximal ring RV pace/sense electrode 38 or the IND_CAN electrode 20 for unipolar pacing and/or sensing. Alternatively, the distal LV CS pace/sense electrode 50 can be paired with the distal tip RV pace/sense electrode 40 for sensing across the RV and LV as described further below. In addition, LV CS lead 52 can comprise a bipolar endocardial lead having an LV ring electrode 58 located proximally to distal tip electrode 50 as shown in FIG. 3 and described further below, so as to allow for maximal flexibility in selection of pacing and sensing electrode pairs for LV pacing and sensing.

Moreover, in a four chamber embodiment, LV CS lead 52 could bear a proximal one or a pair of LA CS pace/sense electrodes positioned along the lead body to lie in the larger diameter coronary sinus CS adjacent the LA. In that case, the lead body 56 would encase two or three electrically insulated lead conductors extending from the more proximal LA CS pace/sense electrode(s) and terminating in a bipolar or tripolar connector 54.

These described RA and LA and RV and LV pace/sense leads and electrode locations are merely exemplary of possible leads and electrode locations that can be employed in the practice of these embodiments of the present invention. It will be understood that one or more of the other types of endocardial and epicardial leads and pace/sense electrodes located in or about the right and left chambers of the heart can be substituted for those illustrated in FIG. 2 and described above.

Typically, in pacing systems of the type illustrated in FIG. 2, the electrodes designated above as "pace/sense" electrodes are used for both pacing and sensing functions. In accordance with one aspect of the present invention, these "pace/sense" electrodes can be selected to be used exclusively as pace or sense electrodes or to be used in common as pace/sense electrodes in programmed combinations for sensing cardiac signals and delivering pacing pulses along pacing and sensing vectors. Separate or shared indifferent pace and sense electrodes can also be designated in pacing and sensing functions. For convenience, the following description separately designates pace and sense electrode pairs.

FIG. 3 depicts atrial and ventricular leads 16, 32, and 52 coupled with an IPG circuit 300 having programmable modes and parameters and a telemetry transceiver of a DDDR type known in the pacing art. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, and the sense amplifiers circuit 360, as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry of cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally the patient's activity level developed in the patient activity sensor (PAS) circuit 322 in the depicted, exemplary IPG circuit 300. The patient activity sensor 316 is coupled to the implantable pulse generator housing 118 and may take the form of a piezoelectric crystal transducer as is well known in the art and its output signal is processed and used as the RCP. A timed interrupt, e.g., every two seconds, may be provided in order to allow the microprocessor 304 to analyze the output of the activity circuit PAS 322 and update the basic V-A (or A-A or V-V) escape interval employed in the pacing cycle Data transmission to and from the external programmer is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. Microprocessor 304 is awakened in response to defined interrupt events, which may include A-PACE, RV-PACE, LV-PACE signals generated by timers in digital timer/controller circuit 330 and A-EVENT, RV-EVENT, and LV-EVENT signals generated by sense amplifiers circuit 360, among others. The specific values of the intervals and delays timed out by digital controller/timer circuit 330 are controlled by the microcomputer circuit 302 by means of data and control bus 306 from programmed-in parameter values and operating modes.

In one embodiment of the invention, microprocessor 304 is a custom microprocessor adapted to fetch and execute instructions stored in RAM/ROM unit 314 in a conventional manner. It is contemplated, however, that other implementations may be suitable to practice the present invention. For example, an off-the-shelf, commercially available microprocessor or microcontroller, or custom application-specific, hardwired logic, or statemachine type circuit may perform the functions of microprocessor 304.

Digital controller/timer circuit 330 operates under the general control of the microcomputer 302 to control timing and other functions within the pacing circuit 320 and includes a set of timing and associated logic circuits of which certain ones pertinent to the present invention are depicted. The depicted timing circuits include discharge/recharge timers 364, V-V delay timer 366, an intrinsic interval timer 368 for timing elapsed V-EVENT to V-EVENT intervals or V-EVENT to A-EVENT intervals, escape interval timers 370 for timing A-A, V-A, and/or V-V pacing escape intervals, an AV delay interval timer 372 for timing an AV delays from a preceding A-EVENT (SAV) or A-PACE (PAV), a post-ventricular timer 374 for timing post-ventricular time periods, and an upper rate interval (URI) timer 376.

Microcomputer 302 controls the operational functions of digital controller/timer circuit 330, specifying which timing intervals are employed, and setting at least the programmed-in base timing intervals, via data and control bus 306. Digital controller/timer circuit 330 starts and times out these intervals and delays for controlling operation of the atrial and ventricular sense amplifiers in sense amplifiers circuit 360 and the atrial and ventricular pace pulse generators in output amplifiers circuit 340.

The post-event timers 374 time out the post-ventricular time periods following an RV-EVENT or LV-EVENT or a RV-PACE or LV-PACE and post-atrial time periods following an A-EVENT or A-PACE. The durations of the post-event time periods may also be selected as programmable parameters stored in the microcomputer 302. The post-ventricular time periods include the PVARP, a post-atrial ventricular blanking period (PAVBP), a ventricular blanking period (VBP), a ventricular refractory period (VRP), and a conditional ventricular refractory period (CVRP). The post-atrial time periods include an atrial refractory period (ARP) during which an A-EVENT is ignored for the purpose of resetting the AV delay, and an atrial blanking period (ABP) during which atrial sensing is disabled. These post-atrial time periods time out concurrently with the time-out of the SAV or PAV delay started by an A-EVENT or an A-PACE.

It should be noted that the starting of the post-atrial time periods and the AV delays can be commenced substantially simultaneously with the start or end of the A-EVENT or A-PACE. Similarly, the starting of the post-ventricular time periods and the V-A escape interval can be commenced substantially simultaneously with the start or end of the V-EVENT or V-PACE.

The microprocessor 304 also optionally calculates AV delays, post-ventricular time periods, and post-atrial time periods which vary with the sensor based escape interval established in response to the RCP(s) and/or with the intrinsic atrial rate. The variable AV delays are usually derived as a fraction of a maximum AV delay set for the pacing lower rate (i.e., the longest escape interval).

The output amplifiers circuit 340 contains a RA pace pulse generator, a RV pace pulse generator and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 330 generates a RV-TRIG or LV-TRIG signal at the end of an AV delay provided by AV delay interval timer 372. Similarly, in order to trigger an atrial pacing or A-PACE pulse, digital controller/timer circuit 330 generates an A-TRIG signal at the end of the V-A escape interval timed by escape interval timers 370. The output amplifiers circuit 340 also includes switching circuits for coupling selected pacing output pairs from among the lead conductors and the IND_CAN electrode 20 to the RA pace pulse generator, RV pace pulse generator and LV pace pulse generator. Pace/sense electrode pair selection and control circuit 350 selects lead conductors and associated pacing electrode pairs to be coupled with the atrial and ventricular output amplifiers within output amplifiers circuit 340 for accomplishing RA, RV and LV pacing as described below.

The sense amplifiers circuit 360 contains sense amplifiers corresponding to any of those presently employed in commercially marketed cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal which is generated across the sense electrode pairs by the passage of a cardiac depolarization. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 controls sensitivity settings of the atrial and ventricular sense amplifiers 360.

The sense amplifiers are uncoupled from the sense electrodes during the blanking periods before, during, and after delivery of a pacing pulse to any of the pace electrodes of the pacing system to avoid saturation of the sense amplifiers. The sense amplifiers circuit 360 includes blanking circuits for uncoupling the selected pairs of the lead conductors and the IND_CAN electrode 20 from the inputs of the RA sense amplifier, RV sense amplifier and LV sense amplifier during the ABP, PVABP and VBP. The sense amplifiers circuit 360 also includes switching circuits for coupling selected sense electrode lead conductors and the IND_CAN electrode 20 to the RA sense amplifier, RV sense amplifier and LV sense amplifier. Again, sense electrode selection and control circuit 350 selects conductors and associated sense electrode pairs to be coupled with the atrial and ventricular sense amplifiers within the output amplifiers circuit 340 and sense amplifiers circuit 360 for accomplishing RA, RV and LV sensing along desired unipolar and bipolar sensing vectors.

Atrial depolarizations or P-waves in the A-SENSE signal that are sensed by an atrial sense amplifier result in an A-EVENT signal that is communicated to the digital controller/timer circuit 330. Ventricular depolarizations or R-waves in the RV-SENSE signal are sensed by a ventricular sense amplifier result in an RV-EVENT signal that is communicated to the digital controller/timer circuit 330. Similarly, ventricular depolarizations or R-waves in the LV-SENSE signal are sensed by a ventricular sense amplifier result in an LV-EVENT signal that is communicated to the digital controller/timer circuit 330. The RV-EVENT, LV-EVENT, and RA-EVENT signals may be refractory or non-refractory, and can inadvertently be triggered by electrical noise signals or aberrantly conducted depolarization waves rather than true R-waves or P-waves.

Figure 4:
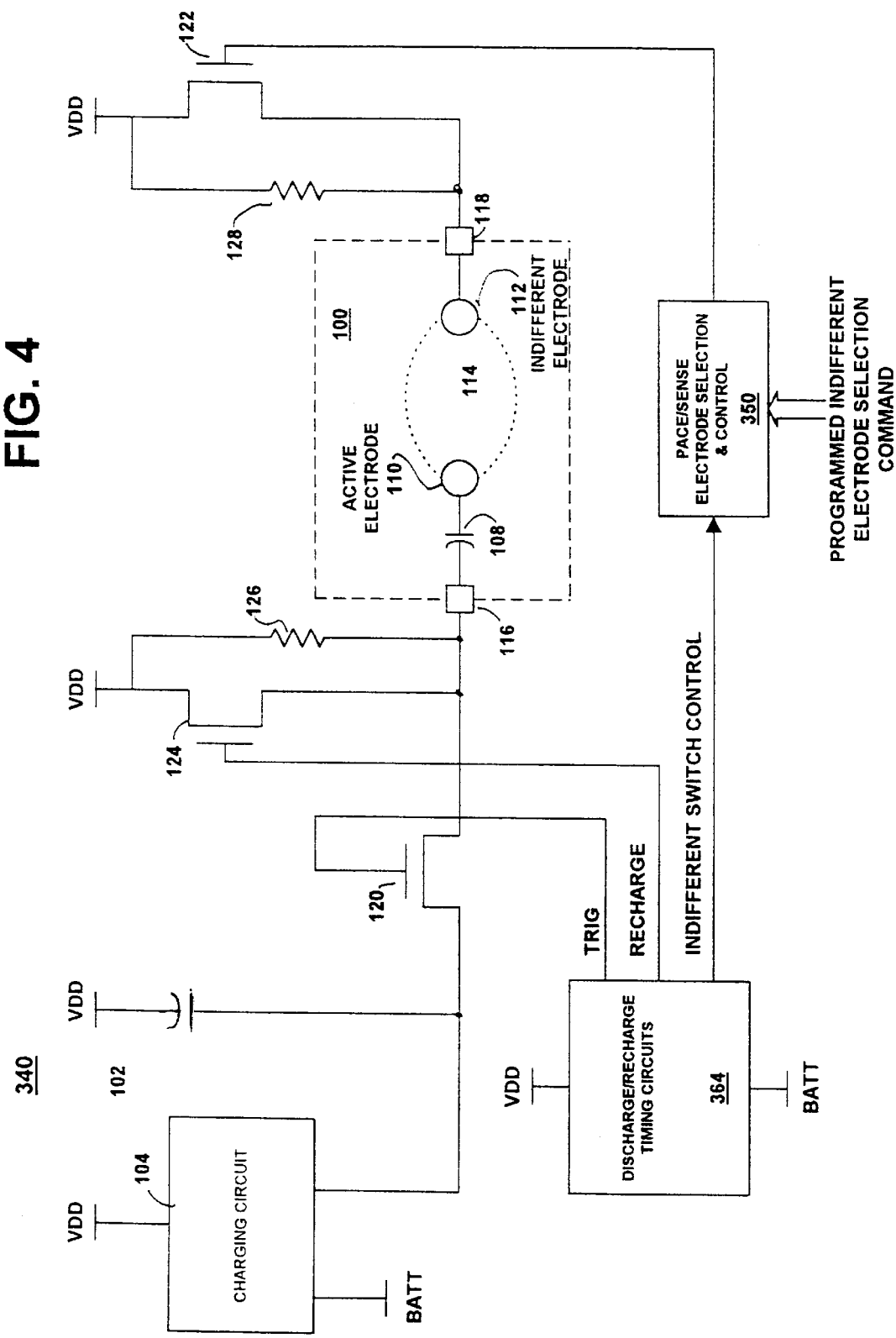
FIG. 4 is a simplified block diagram of components of the IPG circuitry of FIG. 3 for delivering a pacing pulse through a pacing path and for recharging a coupling capacitance of the pacing path following delivery of the pacing pulse.

FIG. 4 is a schematic block diagram illustrating certain components of each of the pacing output amplifiers that are included within output amplifiers circuit 340 and the pacing path 100 that effect the delivery of the A-PACE, RV-PACE and LV-PACE and the recharging of the pacing path load impedance thereafter. An output capacitor 102 is included in each such pacing output amplifier and is charged to a regulated or unregulated voltage by a charging circuit 104 in a manner described in detail in commonly assigned U.S. Pat. No. 5,387,228, incorporated herein by reference. The output capacitor 102 is discharged through the pacing path 100 when a TRIG signal and an indifferent switch control signal are supplied by the discharge/recharge timing circuits 364 for the pacing pulse width $t_{pw}$ of FIG. 1. The pacing path 100 is recharged when a RECHARGE signal and an indifferent switch control signal are generated during the recharge time period $t_r$ of FIG. 1. Pace/sense electrode selection and control 350 routes the indifferent switch control signal to close a FET switch for a particular indifferent electrode that is programmed by the physician for the pace electrode pair in each pacing path 100.

The pacing path 100 comprises the coupling capacitor 108, the active tip electrode 110 (which may be tip electrodes 19, 40 or 50 of FIGS. 2 and 3), the indifferent electrode 112 (which may be any of the indifferent can 20 or ring electrodes 21, 38 and 58) and the body tissue 114 between the active and indifferent electrodes 110 and 1 12. The impedance load across the output amplifier terminals 116 and 118 comprises the impedance of the lead conductor (s), the tissue-electrode interface impedances, and the impedance of the body tissue 114 between the active and indifferent electrodes 110 and 112.

Each output amplifier comprises an output capacitor 102, discharge FET 120, and an active electrode 110 that is coupled through the coupling capacitor 108 and output terminal 116 to the discharge FET 120. The pacing path 100 is completed by the programmed selection of the indifferent electrode 112.

When the output capacitor 102 is to be discharged through the pacing path to deliver a pacing pulse to the pacing path 100, the TRIG (which may be an A-TRIG, RV-TRIG or LV-TRIG of FIG. 3) and indifferent switch control signals are generated for the pacing pulse width time $t_{pw}$. The indifferent electrode switch 122 is closed by pace/sense electrode selection and control 350, and the TRIG signal closes the discharge FET 120. The voltage on output capacitor 102 is discharged through the pacing path 100, resulting in charging of the series connected coupling capacitor 108 and the polarization of the other reactive impedances of the pacing path 100.

The RECHARGE signal is generated after the delay $t_{dpt}$ of FIG. 1 and applied to the RECHARGE FET 124 to close it for the recharge time $t_r$. The polarization after potentials dissipate through the recharge path comprising the pacing path 100, the RECHARGE FET 124 and the resistors 126 and 128. The RECHARGE signal is modulated to regulate the conductivity of the FET 124 to maintain the recharge voltage $V_r$ within a desired range.

Typically, the recharge time period $t_r$ is on the order of 10–30 msec. The recharge operations of the present invention come into play when bi-chamber pacing is invoked to deliver right and left heart chamber pacing pulses that are separated by a triggered pacing delay that overlaps the recharge time period. The present invention is of particular use in the bi-ventricular pacing system of FIGS. 2 and 3 as described further below. However, it may be of use in any other pacing systems or any human tissue stimulator that delivers pairs or trains of stimulation pulses that are closely coupled together and require recharging of the discharge path.

Figure 5:
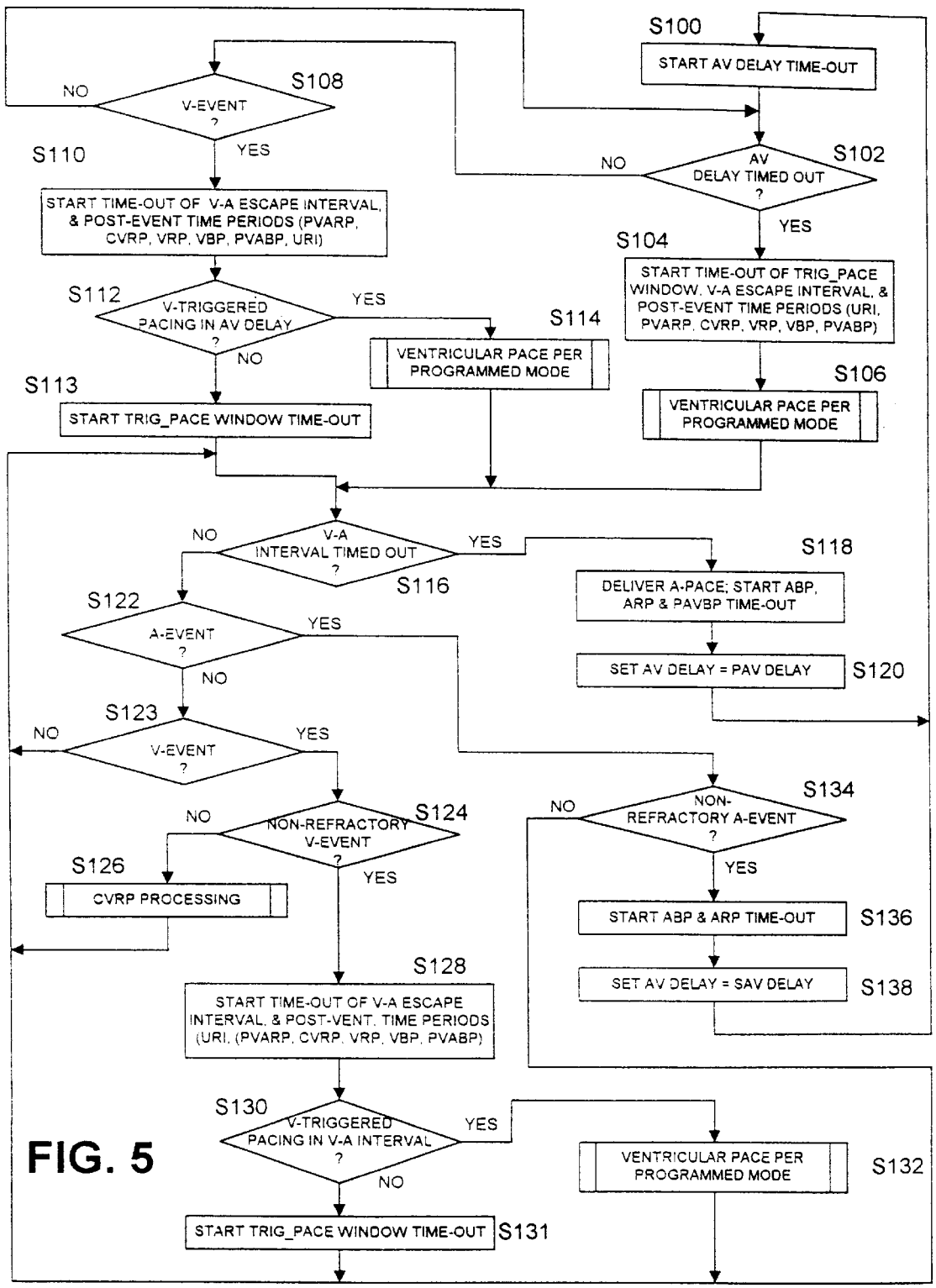
FIG. 5 is a comprehensive flow-chart illustrating the operating modes of the IPG circuitry of FIG. 3.

In the preferred embodiment of the present invention, the general operation of IPG circuit 300 depicted in the flow chart of FIG. 5 is first described. The AV delay is started in step S100 when a P-wave outside of refractory is sensed across the selected RA sense electrodes (or LA sense electrodes if present) during the V-A escape interval (an A-EVENT) as determined in step S134 or an A-PACE pulse is delivered to the selected atrial pace electrode pair in step S118. The AV delay can be a PAV or SAV delay, depending upon whether it is started on an A-PACE or an A-EVENT, respectively, and is timed out by the SAV/PAV delay timer 372. The SAV or PAV delay is terminated upon a non-refractory RV-EVENT or LV-EVENT output by a ventricular sense amplifier prior to its time-out.

The post-event timers 374 are started to time out the post-ventricular time periods and the TRIG_PACE window, and the V-A escape interval timer 370 is started to time out the V-A escape interval in step S104 if the SAV or PAV delay times out in step S102 without the detection of a non-refractory RV-EVENT or LV-EVENT. The TRIG_PACE window inhibits triggered pacing modes in response to a sense event occurring too early in the escape interval and is described in greater detail in the above-referenced Ser. No. 09/439,078 application.

Either a programmed one or both of the RV-PACE and LV-PACE pulses are delivered in step S106 (as shown in FIG. 5) to selected RV and LV pace electrode pairs, and the V-A escape interval timer is timed out in step S116. When both of the RV-PACE and LV-PACE pulses are delivered, the first is referred to as V-PACE1, the second is referred to as V-PACE2, and they are separated by a VP-VP delay. As described in greater detail below in reference to FIGS. 6A–6B, if a bi-ventricular pacing mode is programmed in step S106, it can be selectively programmed in a left-to-right or right-to-left ventricle pacing sequence wherein the first and second delivered ventricular pacing pulses are separated by separately programmed VP-VP delays. The VP-VP delays are preferably programmable between nearly 4 msec and about 80 msec.

Figure 7B:
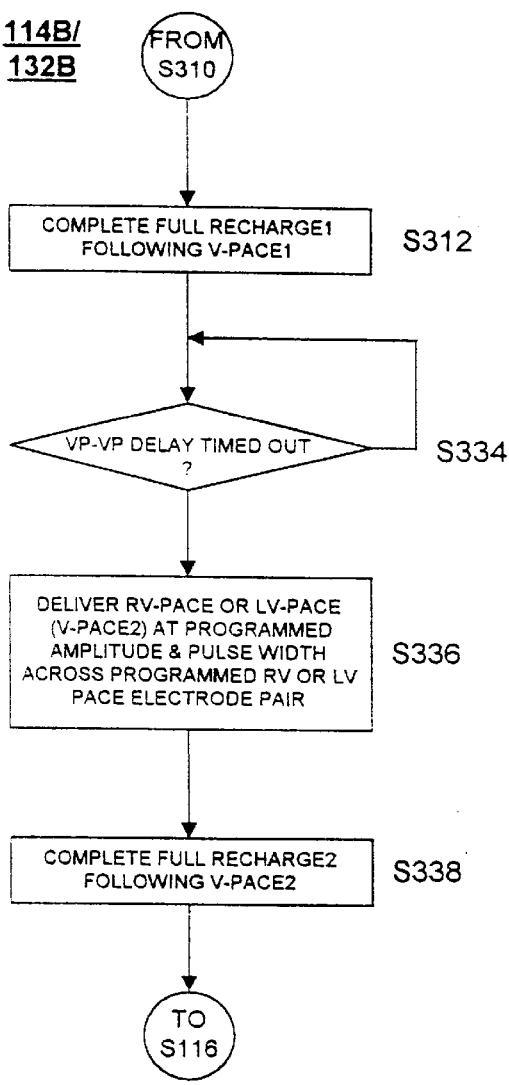

Returning to step S102, the AV delay is terminated if an RV-EVENT or LV-EVENT (collectively, a V-EVENT) is generated by the RV sense amplifier or the LV sense amplifier in step S108. The time-out of the V-A escape interval and the post-ventricular time periods are started in step S110 in response to the V-EVENT. In step S112, it is determined whether a ventricular triggered pacing mode is programmed to be operative during the AV delay. If one is programmed on, then it is undertaken and completed in step S114 (FIGS. 7A–7B). If a ventricular triggered pacing mode is not programmed on as determined in step S112, then no ventricular pacing is triggered by a sensed non-refractory V-EVENT terminating the AV delay. The time-out of the TRIG_PACE window is commenced in step S113 simultaneously with the time-out of the V-A escape interval and post-event time periods in step S110.

If the V-A atrial escape interval is timed out by timer 370 in step S116 without a non-refractory A-EVENT being sensed across the selected pair of atrial sense electrodes, then the A-PACE pulse is delivered across the selected RA pace electrode pair in step S118. The AV delay is set to PAV in step S120, and the AV delay is commenced by AV delay timer 372.

If a non-refractory A-EVENT is generated as determined in steps S122 and S134, then the V-A escape interval is terminated. The ABP and ARP are commenced by post-event timers 374 in step SI 34, the AV delay is set to the SAV in step S138, and the SAV delay is started in step S100 and timed out by SAV/PAV delay timer 372.

Assuming that the normal activation sequence is sought to be restored, a programmed SAV and PAV delay corresponding to a normal AV conduction time from the AV node to the bundle of His are used or a calculated SAV and PAV delay is calculated in relation to the prevailing sensor rate or sensed intrinsic heart rate and are used by SAV/PAV delay timer 372.

If an RV-EVENT or LV-EVENT or a collective V-EVENT sensed across the RV tip sense electrode and the LV sense electrode (for simplicity, all referred to as a V-EVENT) is detected in step S123 during the time-out of the V-A escape interval, then, it is determined if it is a non-refractory V-EVENT or a refractory V-EVENT in step S124. If the V-EVENT is determined to be a refractory V-EVENT in step S124, then it is employed in the CVRP processing step S126 as disclosed in the above-referenced Ser. No. 09/439, 244application. If the V-EVENT is determined to be a non-refractory V-EVENT in step S124, then the V-A escape interval and the post-ventricular time periods are restarted in step S128.

Figure 6B:
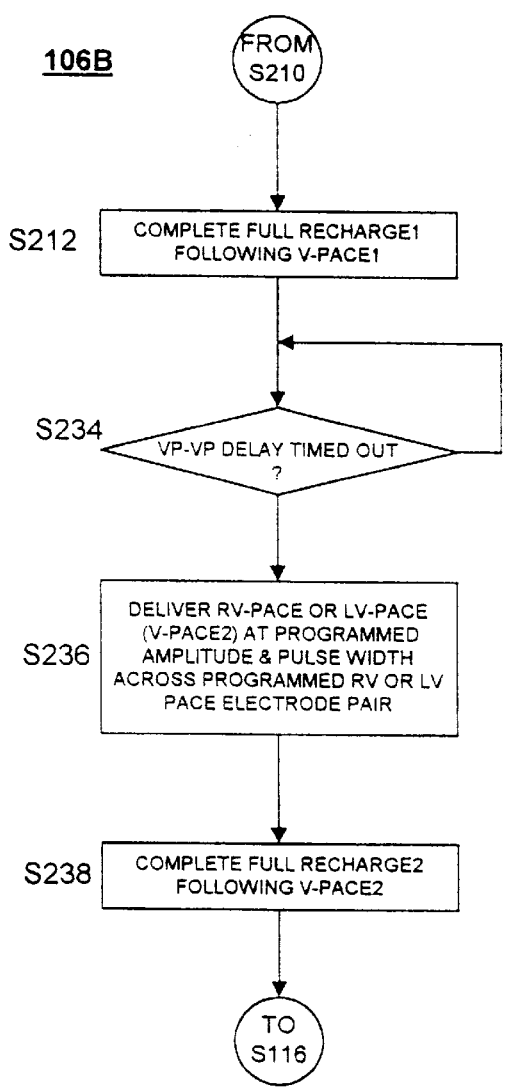

In step S130, it is determined whether a triggered pacing mode is programmed to be operative during the V-A escape interval. If one is programmed on, then it is undertaken and completed in step S132 (FIGS. 6A–6B). If triggered pacing is not programmed on as determined in step S130, then no ventricular pacing is triggered by the sensed non-refractory V-EVENT during the V-A escape interval. The time-out of the TRIG_PACE window is commenced in step S131 simultaneously with the time-out of the V-A escape interval and post-event time periods in step S128.

FIGS. 6A–6B depicts the step S106 in greater detail, and FIGS. 7A–7B depict the steps S114 and S132 in greater detail. As described in greater detail below, if a bi-ventricular VP-VP pacing mode is programmed on in step S106, it can be selectively programmed in a left-to-right or right-to-left ventricle sequence, wherein the first and second delivered ventricular pacing pulses (V-PACE1 and V-PACE2) are separated by separately programmed VP-VP delays. If a bi-ventricular triggered pacing mode is programmed on in either or both of steps S114 and S132, it can be selectively programmed to immediately pace the ventricle from which the V-EVENT is sensed or a fixed or programmed ventricle regardless of where the V-EVENT is sensed with a V-PACE1. Then, the V-PACE2 is generated to synchronously pace the other ventricle after a programmed VS/VP-VP delay. Or, the triggered pacing mode can be selectively programmed in either or both of steps S114 and 132 to only synchronously pace the other ventricle than the ventricle from which the V-EVENT is sensed with V-PACE2 after separately programmable VS-VP delays, depending on the right-to-left or left-to-right sequence. All of these VP-VP, VS/VP-VP, and VS-VP delays are preferably programmable between nearly 0 msec and about 80 msec.

As a practical matter, the minimum VS/VP-VP, and VP-VP delay may be set to one half the system clock cycle in order to avoid simultaneous delivery of RV-PACE and LV-PACE pulses. The pacing pulse width is typically programmable between about 0.5 msec and 2.0 msec, and the pacing pulse amplitude is typically programmable between 0.5 and 7.5 volts. The system clock provides a full clock cycle of about 8.0 msec. Therefore, the minimum VP-VP delay is set at a half clock cycle or about 4.0 msec.

It is desired to be able to deliver RV-PACE and LV-PACE pulses that differ from one another in pulse width and amplitude in order to make certain that the delivered energy is sufficient to capture the heart chamber without being unduly wasteful of energy. But, if differing amplitude and pulse width RV-PACE and LV-PACE pulses are simultaneously delivered to the right and left ventricles, then DC current pathways can develop between the active electrodes that can cause aberrant conduction pathways in the heart and can lead to oxidation or other deterioration of the pace/sense electrodes.

In addition, when a pacing system is implanted, the physician undertakes a work-up of the patient to determine the pacing energy and sensing thresholds that are sufficient to capture the heart and to distinguish true P-waves and R-waves from muscle artifacts and ambient electrical noise. If LV-PACE and RV-PACE pulses are delivered simultaneously, there may be a current contribution from the highest voltage active electrode delivering the highest voltage pulse to the lower voltage active electrode delivering the lower voltage pulse. The contribution may be sufficient to lower the pacing threshold at the lowest voltage active electrode. Then, at a later time, the programmed mode may be changed by eliminating or lowering the voltage of the highest voltage pacing pulse, and capture may be lost at the lowest voltage active pacing electrode.

Figure 8:
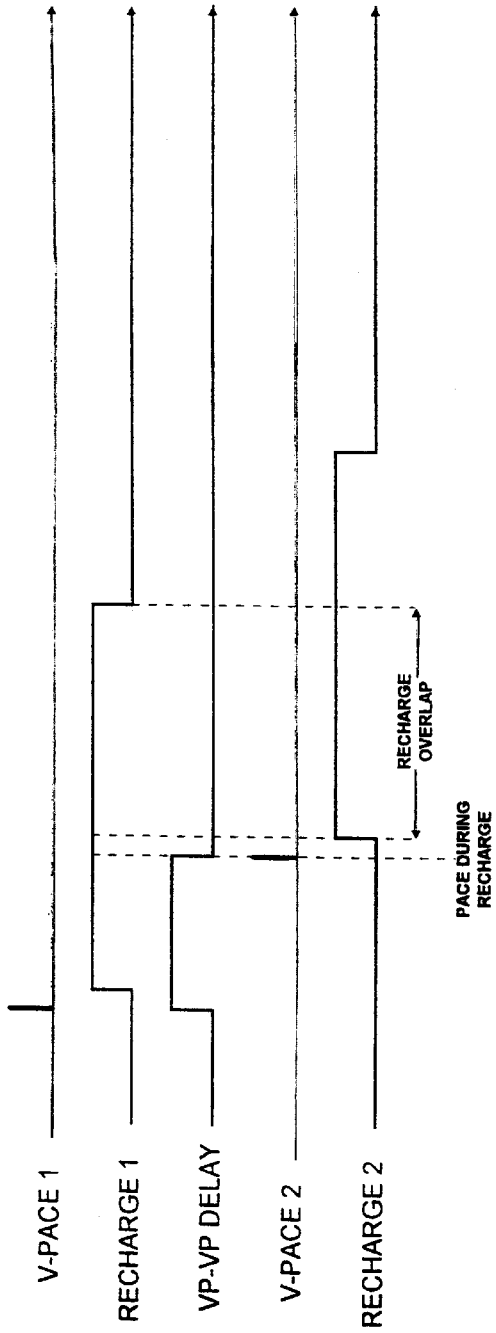
FIG. 8 is a timing chart illustrating error conditions arising during delivery of closely spaced pacing pulses and recharging in accordance with FIG. 1.
Figure 9:
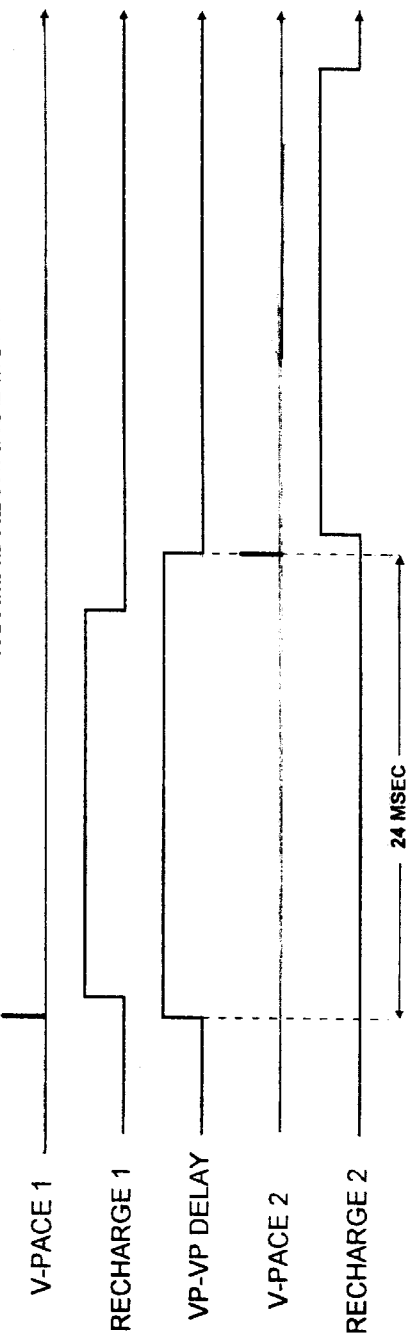

Moreover, other problems arise when recharging is conducted simultaneously following V-PACE 1 and V-PACE2 under certain combinations of pacing paths and pacing pulse energies. And, problems can arise if V-PACE2 is delivered during the recharge of the pacing path that V-PACE1 was delivered into. FIG. 8 illustrates these error conditions that can occur if a normal recharge sequence of RECHARGE1 following V-PACE1 and RECHARGE2 following V-PACE2. Consequently, the present invention offers alternative recharge regimens for the V-PACE1–V-PACE2 scenarios under certain conditions as set forth in the steps of FIGS. 6 and 7A–7B and as illustrated in FIGS. 9–12.

FIGS. 6A–6B are a flow chart illustrating step S106 in greater detail enabling the delivery of single or triggered ventricular pacing pulses following time-out of an AV delay in step S102. The IPG circuit 300 of FIG. 3 can be programmed to either only deliver a single RV-PACE or LV-PACE or the pair of RV-PACE and LV-PACE pulses separated by the VP-VP delay timed out by V-V delay timer 366. If delivery of only a single RV-PACE or LV-PACE is programmed as determined in step S200, then it is delivered in step S202. The pacing pulse is typically delivered across the active or cathode RV or LV tip electrodes 40 or 50 and one of the available indifferent electrodes that is programmed and selected through the pace electrode selection and control 350 depending upon which are present in the pacing system and the pacing vector that is desired. The indifferent electrodes depicted in FIG. 3 include the IND_ RV electrode 38, the IND_CAN electrode 20, and the IND_LV electrode 58. Although one of the RV or LV tip electrodes 40 or 50 RV could be programmed to be the active electrode and the other the indifferent electrode, it is generally not desirable to do so since both are of relatively small surface area, and it is usually desirable to provide a relatively large indifferent electrode surface area.

If only a single LV-PACE or RV-PACE pulse is delivered in step S202, then the recharge of the single pacing path takes place in the normal manner in step S204.

If VP-VP pacing is programmed on in step S200, then V-PACE1 is delivered in step S206 in the programmed RV-LV or LV-RV sequence. Again, the pacing pulse is typically delivered across the active, cathode RV or LV tip electrodes 40 or 50 and one of the available indifferent electrodes that is programmed and selected through the pace electrode selection and control 350 depending upon which are present in the pacing system and the pacing vector that is desired as set forth above. V-PACE1 is delivered at a programmed pulse energy dictated by the programmed voltage and pulse width.

The V-A escape interval and the post-ventricular time periods are timed out in timers 370 and 374 in step s208. The V-V delay timer 366 is also loaded with the programmed VP-VP delay and starts to time out in step S208.

If the RV-PACE pulse is V-PACE1, then a programmed VP-VP delay is timed in V-V delay timer 366. The LV-PACE pulse is delivered as V-PACE2 typically across the active LV pace electrode 50 and the programmed indifferent electrode in step S222 after time-out of the programmed VP-VP delay in step S218. Conversely, if the LV-PACE pulse is the first to be delivered as V-PACE1, then a programmed VP-VP delay is timed in V-V delay timer 366. The RV-PACE pulse is then delivered as V-PACE2 typically across the active RV pace electrode 40 and the programmed indifferent electrode in step S222 of FIG. 6A or S236 of FIG. 6B after time-out of the programmed VP-VP delay as determined in step S218 of FIG. 6A or step S234 of FIG. 6B.

In addition, other steps are taken to govern the RECHARGE1 and RECHARGE2 sequences as illustrated in FIGS. 8-12. In step S210, the VP-VP delay is compared to the RECHARGE1 period. Typically, the RECHARGE1 and RECHARGE 2 periods are about 20 msec, and the VP-VP delays are programmable between 4–80 msec in 4 msec increments as shown in FIGS. 8–12. Thus, if the VP-VP delay is 24 msec or more, then, the normal recharge sequence illustrated in FIG. 9 can be followed in steps S212 and S234–S238 of FIG. 6B. In this case, RECHARGE 1 is commenced and completed in step S210, the VP-VP delay times out in step S234, V-PACE2 is delivered in step S236, and RECHARGE2 is commenced and completed in step S238. The program loops back to step S116 after RECHARGE2 is completed in step S238 since RECHARGE1 was already completed in step S218. Thus, these steps provide for sequential RECHARGE1 and RECHARGE2 if the VP-VP delay exceeds the RECHARGE1.

FIGS. 10–12 illustrate three possible alternative recharge timing modes that can be undertaken if the VP-VP delay is less than the RECHARGE1 period as determined in step S210. These recharge modes include a truncated mode, a postponed & sequential mode, and a simultaneous mode. It will be understood that in a simpler algorithm, step S210 and the steps of FIG. 6B could be eliminated so that one of the three possible alternative recharge timing modes illustrated in FIGS. 10–12 could be followed regardless of the length of the VP-VP delay.

FIG. 10 illustrates the truncated recharge mode, wherein RECHARGE1 is commenced after V-PACE 1, suspended prior to delivery of V-PACE2 and for the duration of RECHARGE2, and is then completed after RECHARGE2. The truncated mode could be used at any programmed VP-VP delay but may be most beneficial when the VP-VP delay is between 8–20 msec, as at the illustrated 8 msec delay. The truncated mode may be programmed on at all times or may be automatically invoked at certain programmed VP-VP delays. RECHARGE1 is commenced in step S216 if the truncated mode is determined to be on step S214. RECHARGE1 is suspended in step S220 when the VP-VP delay is determined to be timed out in step S218 and before the delivery of V-PACE2 in step S222. Then, steps S226–S230 are followed to resume and complete RECHARGE1 after RECHARGE2 is completed in step S224.

FIG. 11 illustrates the postponed and sequential recharge mode, wherein RECHARGE1 is postponed after V-PACE1 and through the delivery of V-PACE2 and for the duration of RECHARGE2, and is then completed after RECHARGE2. The postponed and sequential recharge mode could be used at any programmed VP-VP delay between 4–20 msec but may be most beneficial when the VP-VP delay is quite short as at the illustrated 4 msec. The postponed and sequential mode is a default mode of the sequence of steps S210 and S214 of FIG. 6A where VP-VP delay is less than the RECHARGE1 period, and the truncated and simultaneous recharge modes are off. RECHARGE1 is not started until step S230 after RECHARGE2 is timed out as determined in step S228.

FIG. 12 illustrates the simultaneous recharge mode, wherein RECHARGE1 is postponed after V-PACE1 and through the delivery of V-PACE2 and then is completed simultaneously with RECHARGE2. The simultaneous recharge mode could be used at any programmed VP-VP delay between 4–20 msec but may be only usable under certain conditions employing common indifferent electrodes and relatively comparable V-PACE1 and V-PACE2 pulse energies. If the simultaneous mode is programmed on in step S226, then RECHARGE1 is commenced and completed in step S232 simultaneously with commencement and completion of RECHARGE2 in step S224.

Both the truncated recharge mode of steps S214, S216 and S220 and the simultaneous recharge mode of steps S226 and S232 could be on, resulting in partial completion of RECHARGE1 during the VP-VP delay in step S216 and full completion in step S232.

FIGS. 7A–7C are a flow chart illustrating the steps S114 and S132 of FIG. 5 for delivering ventricular pacing pulses triggered by a ventricular sense event in step S108 during the time-out of an AV delay or in step S124 during time-out of the V-A escape interval. As noted above, the sensing of R-waves in the RV and LV can be accomplished employing several RV-SENSE and LV-SENSE sensing axes or vectors. A bipolar RV-SENSE vector (RV sense electrodes 38 and 40), a unipolar RV-SENSE vector (RV tip sense electrode 40 and IND_CAN electrode 20), and a unipolar LV-SENSE vector (LV sense electrode 50 and IND_CAN electrode 20), a bipolar LV-SENSE vector (LV sense electrodes 50 and 58), and a trans-ventricular, combined RV-SENSE and LV-SENSE vector (RV tip sense electrode 40 and LV sense electrode 50) can be programmed. The selection of the sensing vectors would depend upon heart condition and the selection of the pacing pulse pathways.

The IPG circuit 300 can be separately programmed in one of three triggered pacing modes designated VS/VP, VS/VP-VP or VS-VP triggered modes for each of steps S114 and S132. In the VS/VP triggered pacing mode, a V-PACE1 is delivered without delay upon a RV-EVENT or LV-EVENT to the RV or LV pacing pathway, respectively. In the VS/VP-VP triggered pacing mode, the V-PACE1 is delivered without delay upon a RV-EVENT or LV-EVENT to the selected RV or LV pacing electrode pair, respectively, and a V-PACE2 is delivered to the other of the selected LV or RV pacing electrode pair after the VS/VP-VP delay times out. In the VS-VP pacing mode, a RV-EVENT or the LV-EVENT starts time-out of a VS-VP delay, and a single pacing pulse (designated V-PACE2) is delivered to the selected LV or the RV pace electrode pair, respectively, when the VS-VP delay times out.

The TRIG_PACE time window started by a prior V-EVENT or V-PACE must have timed out in step S300 prior to delivery of any triggered ventricular pacing pulses. If it has not timed out, then triggered pacing cannot be delivered in response to a sensed V-EVENT. If the TRIG_PACE window has timed out, it is then restarted in step S302, and the programmed triggered pacing modes are checked in steps S304 and S334.

When IPG circuit 300 is programmed in the VS/VP-VP triggered mode as determined in step S304, the RV-EVENT or LV-EVENT triggers the immediate delivery of an RV-PACE or an LV-PACE across the programmed bipolar or unipolar RV and LV pace electrode pair, respectively, in step S308. Then, a VS/VP-VP delay is started in step S308 and timed out in step S318 of FIG. 7A or step S334 of FIG. 7B. The VS/VP-VP delay is specified as a VP-VP delay when the RV-EVENT is sensed and the RV-PACE is V-PACE1 and the LV-PACE is V-PACE2. The VS/VP-VP delay is specified as a VP-VP delay when the LV-EVENT is sensed and the LV-PACE is V-PACE1 and the RV-PACE is V-PACE2. The LV-PACE or RV-PACE pulse is delivered at the programmed amplitude and pulse width across the programmed LV or RV pace electrode pair in step S322.

The VS/VP-VP sequence of operation is substantially the same as the VP-VP triggered pacing mode illustrated in FIGS. 6A and 6B and described above. FIG. 7A also illustrates the steps S314–S332 for performing the truncated recharge mode of FIG. 10, the postponed and sequential mode of FIG. 11 and the simultaneous recharge mode of FIG. 12 in the same manner as described above with respect to FIGS. 6A–6B. FIG. 7B illustrates the steps S312 and S334–S338 for performing the normal recharge mode of FIG. 9 if the VS/VP-VP delay exceeds RECHARGE1 as determined in step S310 of FIG. 7A.

If the VS/VP-VP triggered pacing mode is not programmed on as determined in step S304, it is determined whether the VS-VP triggered pacing mode or the VS/VP triggered pacing mode is programmed on in steps S340 and S341 of FIG. 7C. When the IPG circuit 300 is programmed to a VS/VP triggered pacing mode, the RV-EVENT or LV-EVENT triggers the immediate delivery of an RV-PACE or an LV-PACE across the programmed bipolar or unipolar RV or LV pace electrode pair, respectively, in step S342.

When the IPG circuit 300 is programmed to the VS-VP triggered pacing mode, an LV-EVENT as determined in step S343 loads the appropriate VS-VP delay in V-V delay timer 366 in step S344 and starts the VS-VP delay time-out in step S345. The RV-PACE is delivered at its time-out in step S346 (also designated V-PACE2). If an RV-EVENT is determined in step S343, then the appropriate VS-VP delay in V-V delay timer 366 in step S348 and the VS-VP delay is timed out in step S350. The LV-PACE (also designated V-PACE2) is delivered at time-out of the VS-VP delay in step S352.

The V-A escape interval is timed out in step S116 following the completion of the ventricular pacing mode of FIGS. 7A–7B for steps S114 and S132. If the V-A escape interval times out, then an RA pace pulse is typically first delivered across the RA pace electrodes 17 and 19 in step S118, and the AV delay timer is restarted in step S100.

It will be understood that other operations ancillary to the typical operation of an AV synchronous pacemaker or a pacemaker operating in a single chamber mode are conducted in the overall operation of a pacing system of this type, that are not necessary to the practice of the present invention. For example, it will be understood that the CVRP operations of the type described in the above-referenced Ser. No. 09/439,244 application can be conducted following the delivery of the V-PACE1 pulses, but they have no effect or play no role in the practice of the present invention.

While the recharge modes of the present invention are described in the context of delivering V-PACE 1 and V-PACE 2 in a variety of pacing paths and right-to left and left-to-right pacing sequences to left and right ventricles in an AV synchronous, atrial synchronous pacemaker, it will be understood that these recharge modes can be employed in a bi-ventricular pacemaker in a like variety of pacing pathways and pacing sequences. In addition, they can be employed to deliver A-PACE1 and A-PACE2 to the right and left atria in a like variety of pacing pathways and pacing sequences. The present invention may advantageously implemented in many of the bi-chamber pacing systems described above, e.g. the systems disclosed in the above-incorporated '324 patent.

The present invention is preferably implemented into an external or implantable pulse generator and lead system selectively employing right and left heart, atrial and/or ventricular leads. The preferred embodiment is implemented in an architecture that allows wide programming flexibility for operating in AV synchronous modes with right and left ventricular pacing or in ventricular only modes for providing only right and left ventricular pacing. It may be implemented into an IPG or external pulse generator and lead system providing both right and left atrial pacing or just right or left atrial pacing and sensing. Alternatively, the invention can be implemented in IPGs or external pulse generators and lead systems having hard wired connections and operating modes that are not as programmable.

The various embodiments of the present invention have been described in terms of a preferred AV synchronous, bi-ventricular pacing system wherein pacing pulses are delivered through a pacing path involving a portion of the human heart. Although it is described in the context of bi-chamber pacing, it will be understood that the same principles of controlling the recharge as shown in FIGS. 9–12 can be applied to multi-site pacing across pacing paths within or embracing the same heart chamber.

In addition, the pacing pulses may be applied to multiple sites in the same or differing heart chambers to treat other cardiac conditions, e.g., treating tachyarrhythmias by closely spaced pacing pulses delivered through a plurality of somewhat overlapping pacing paths.

It will also be appreciated that the stimulation energy may be other than a pacing pulse, and that the stimulation path may constitute other living body tissue stimulated at multiple sites in a sequential fashion, e.g., nerve, bladder, sphincter, brain, and other organs or muscle groups. The problems of recharging any reactive living body tissue stimulation path to enable closely spaced delivery of stimulation pulse energy can be addressed in the manner described above.

The preceding specific embodiments are illustrative of the practice of the invention. It is to be understood, therefore, that other expedients known to those of skill in the art or disclosed herein may be employed.

It will be understood that certain of the above-described structures, functions and operations of the pacing systems of the preferred embodiments are not necessary to practice the present invention and are included in the description simply for completeness of an exemplary embodiment or embodiments. It will also be understood that there may be other structures, functions and operations ancillary to the typical operation of such pacing systems that are not disclosed and are not necessary to the practice of the present invention. In addition, it will be understood that specifically described structures, functions and operations set forth in the above-listed, commonly assigned and co-pending patent applications can be practiced in conjunction with the present invention, but they are not essential to its practice.

In the following claims, means-plus-function clauses are intended to cover the structures described herein as performing the recited function and not only structural equivalents but also equivalent structures.

It is therefore to be understood, that within the scope of the appended claims, the invention may be practiced otherwise than as specifically described without actually departing from the spirit and scope of the present invention.

What is claimed is:

1. A method of repetitively delivering first and second closely spaced electrical stimulation pulses to living tissue through first and second reactive stimulation paths and for recharging the stimulation paths to alleviate polarization after potentials prior to delivery of subsequent stimulation pulses to the same stimulation paths comprising the steps of:

applying said first stimulation pulse to a first stimulation path;

timing a trigger delay from said first stimulation pulse;

applying said second stimulation pulse to a second stimulation path upon time-out of said trigger delay; and recharging said first and second stimulation paths for predetermined recharge time periods following application of said second stimulation pulse to said second stimulation path.

2. The method of claim 1, wherein said recharging step further comprises the step of:

sequentially recharging said first and second stimulation paths during first and second recharge time periods.

3. The method of claim 1, wherein said recharging step further comprises the steps of:

recharging said second stimulation path for a predetermined recharge time period following application of said second stimulation pulse to said second stimulation path; and recharging said first stimulation path for a predetermined recharge time period following recharging of said second stimulation path.

4. The method of claim 1, wherein said recharging step further comprises the step of:

simultaneously recharging said first and second stimulation paths.

5. The method of claim 1, wherein said recharge time periods exceed said trigger delay, and said recharging step further comprises the steps of:

recharging said second stimulation path for a predetermined recharge time following application of said second stimulation pulse to said second stimulation path; and recharging said first stimulation path for a predetermined recharge time following recharging of said second stimulation path.

6. The method of claim 1, further comprising the step of:

during the timing of said trigger delay from said first stimulation pulse, recharging said first stimulation path for predetermined truncated recharge time period less than said trigger delay.

7. The method of claim 6, wherein said recharging step further comprises the steps of:

recharging said second stimulation path for a single recharge time period following application of said second stimulation pulse to said second stimulation path; and recharging said first stimulation path for a further recharge time period following recharging of said second stimulation path.

8. Apparatus for repetitively delivering first and second closely spaced electrical stimulation pulses to living tissue through first and second reactive stimulation paths and for recharging the stimulation paths to alleviate polarization after potentials prior to delivery of subsequent stimulation pulses to the same stimulation paths, the apparatus comprising:

means for applying said first stimulation pulse to a first stimulation path;

means for timing a trigger delay from said first stimulation pulse;

means for applying said second stimulation pulse to a second stimulation path upon time-out of said trigger delay; and means for recharging said first and second stimulation paths for predetermined recharge time periods following application of said second stimulation pulse to said second stimulation path.

9. The apparatus of claim 8, wherein said recharging means further comprises:

means for sequentially recharging said first and second stimulation paths during first and second recharge time periods.

10. The apparatus of claim 8, wherein said recharging means further comprises:

means for recharging said second stimulation path for a predetermined recharge time period following application of said second stimulation pulse to said second stimulation path; and means for recharging said first stimulation path for a predetermined recharge time period following recharging of said second stimulation path.

11. The apparatus of claim 8, wherein said recharging means further comprises:

means for simultaneously recharging said first and second stimulation paths.

12. The apparatus of claim 8, wherein said recharge time periods exceed said trigger delay, and said recharging means further comprises:

means for recharging said second stimulation path for a predetermined recharge time following application of said second stimulation pulse to said second stimulation path; and means for recharging said first stimulation path for a predetermined recharge time following recharging of said second stimulation path.

13. The apparatus of claim 8, further comprising:

means for during the timing of said trigger delay from said first stimulation pulse, recharging said first stimulation path for predetermined truncated recharge time period less than said trigger delay.

14. The apparatus of claim 13, wherein said recharging means further comprises:

means for recharging said second stimulation path for a single recharge time period following application of said second stimulation pulse to said second stimulation path; and means for recharging said first stimulation path for a further recharge time period following recharging of said second stimulation path.

15. A method of repetitively delivering first and second closely spaced pacing pulses through first and second reactive pacing paths of the heart and for recharging the pacing paths to alleviate polarization after potentials prior to delivery of subsequent pacing pulses to the same pacing paths comprising the steps of:

applying said first pacing pulse to a first pacing path;

timing a trigger delay from said first pacing pulse;

applying said second pacing pulse to a second pacing path upon time-out of said trigger delay; and recharging said first and second pacing paths for predetermined recharge time periods following application of said second pacing pulse to said second pacing path.

16. The method of claim 15, wherein said recharging step further comprises the step of:

sequentially recharging said first and second pacing paths during first and second recharge time periods.

17. The method of claim 15, wherein said first pacing path is across one of the right and left ventricles and the second pacing path is the other of the right and left ventricles.

18. The method of claim 15, wherein said recharging step further comprises the steps of:

recharging said second pacing path for a predetermined recharge time period following application of said second pacing pulse to said second pacing path; and recharging said first pacing path for a predetermined recharge time period following recharging of said second pacing path.

19. The method of claim 15, wherein said recharging step further comprises the step of:

simultaneously recharging said first and second pacing paths.

20. The method of claim 15, wherein said recharge time periods exceed said trigger delay, and said recharging step further comprises the steps of:

recharging said second pacing path for a predetermined recharge time following application of said second pacing pulse to said second pacing path; and recharging said first pacing path for a predetermined recharge time following recharging of said second pacing path.

21. The method of claim 15, further comprising the step of:

during the timing of said trigger delay from said first pacing pulse, recharging said first pacing path for predetermined truncated recharge time period less than said trigger delay.

22. The method of claim 21, wherein said recharging step further comprises the steps of:

recharging said second pacing path for a single recharge time period following application of said second pacing pulse to said second pacing path; and recharging said first pacing path for a further recharge time period following recharging of said second pacing path.

23. Apparatus for repetitively delivering first and second closely spaced electrical pacing pulses through first and second reactive pacing paths of the heart and for recharging the pacing paths to alleviate polarization after potentials prior to delivery of subsequent pacing pulses to the same pacing paths, the apparatus comprising:

means for applying said first pacing pulse to a first pacing path;

means for timing a trigger delay from said first pacing pulse;

means for applying said second pacing pulse to a second pacing path upon time-out of said trigger delay; and means for recharging said first and second pacing paths for predetermined recharge time periods following application of said second pacing pulse to said second pacing path.

24. The apparatus of claim 23, wherein said recharging means further comprises:

means for sequentially recharging said first and second pacing paths during first and second recharge time periods.

25. The apparatus of claim 23, wherein said recharging means further comprises:

means for recharging said second pacing path for a predetermined recharge time period following application of said second pacing pulse to said second pacing path; and means for recharging said first pacing path for a predetermined recharge time period following recharging of said second pacing path.

26. The apparatus of claim 23, wherein said recharging means further comprises:

means for simultaneously recharging said first and second pacing paths.

27. The apparatus of claim 23, wherein said recharge time periods exceed said trigger delay, and said recharging means further comprises:

means for recharging said second pacing path for a predetermined recharge time following application of said second pacing pulse to said second pacing path; and means for recharging said first pacing path for a predetermined recharge time following recharging of said second pacing path.

28. The apparatus of claim 23, further comprising:

means for during the timing of said trigger delay from said first pacing pulse, recharging said first pacing path for predetermined truncated recharge time period less than said trigger delay.

29. The apparatus of claim 28, wherein said recharging means further comprises:

means for recharging said second pacing path for a single recharge time period following application of said second pacing pulse to said second pacing path; and means for recharging said first pacing path for a further recharge time period following recharging of said second pacing path.

30. The apparatus of claim 23, wherein said first pacing path is across one of the right and left ventricles and the second pacing path is the other of the right and left ventricles.

* * * * *